(12) United States Patent
Plaian et al.

(10) Patent No.: US 11,412,927 B2
(45) Date of Patent: Aug. 16, 2022

(54) EYE FUNDUS INSPECTION APPARATUS

(71) Applicant: CENTERVUE S.P.A., Padua (IT)

(72) Inventors: Andrei Plaian, Noventa Padovana (IT); Irene Mogentale, Due Carrare (IT)

(73) Assignee: CENTERVUE S.P.A., Padua (IT)

( * ) Notice: Subject to any disclaimer, the term of this patent is extended or adjusted under 35 U.S.C. 154(b) by 488 days.

(21) Appl. No.: 16/619,743

(22) PCT Filed: Jun. 26, 2018

(86) PCT No.: PCT/EP2018/067050
§ 371 (c)(1),
(2) Date: Dec. 5, 2019

(87) PCT Pub. No.: WO2019/002256
PCT Pub. Date: Jan. 3, 2019

(65) Prior Publication Data
US 2020/0205658 A1    Jul. 2, 2020

(30) Foreign Application Priority Data

Jun. 27, 2017  (IT) .......................... 102017000071789

(51) Int. Cl.
  *A61B 3/12*    (2006.01)
  *A61B 3/00*    (2006.01)
  *A61B 5/00*    (2006.01)
  *A61B 3/10*    (2006.01)
(52) U.S. Cl.
  CPC .............. *A61B 3/12* (2013.01); *A61B 3/0008* (2013.01); *A61B 5/0068* (2013.01); *A61B 5/0071* (2013.01)

(58) Field of Classification Search
  None
  See application file for complete search history.

(56) References Cited

U.S. PATENT DOCUMENTS

| 4,213,678 A * | 7/1980 | Pomerantzeff ....... A61B 3/1025 351/221 |
| 2010/0128221 A1 | 5/2010 | Muller et al. |
| 2021/0290050 A1* | 9/2021 | Shiba ....................... A61B 3/12 |

FOREIGN PATENT DOCUMENTS

| JP | 2016041222 A | 3/2016 |
| WO | 2016037980 A1 | 3/2016 |

* cited by examiner

*Primary Examiner* — Hung Q Dang
(74) *Attorney, Agent, or Firm* — Patterson Intellectual Property Law, P.C.

(57) ABSTRACT

Eye fundus inspection apparatus (500) comprising: —illumination means (12) comprising at least a light source (121, 123, 124, 126) and adapted to project a first light beam (1) towards a retina (101) of an eye (100); —an optical lighting path (1A) for said first light beam; —acquisition means (27) adapted to receive a second light beam (2) coming from the retina; —an optical acquisition path (2A) for said second light beam; —scanning means (17) adapted to scan said first light beam (1) on the retina with a linear movement, according to a first scanning direction (S1), or with a circular movement about a rotation axis (A), according to a second scanning direction (S2); —light beam separating means (16) adapted to define separate passage zones for said first and second light beams (1, 2) at a pupil of the eye; —a control unit (120) adapted to control operation of said inspection apparatus; —first light beam shaping means (11) and second light beam shaping means (23, 271, 272) that allow obtaining improved retinal images.

20 Claims, 12 Drawing Sheets

Figure 1:
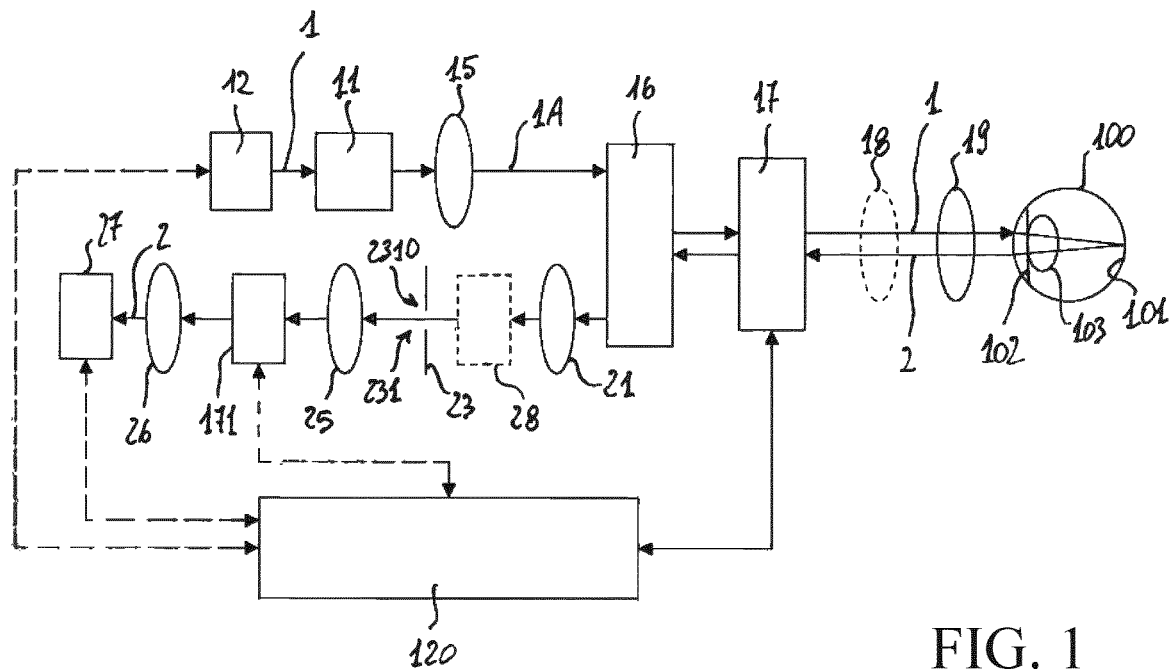

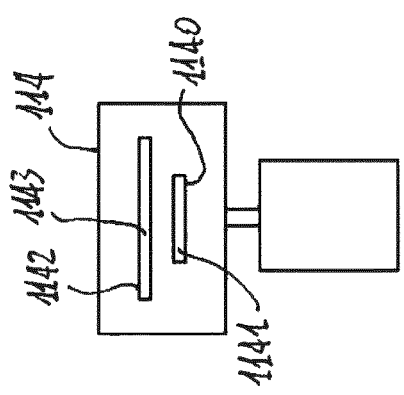
FIG. 8
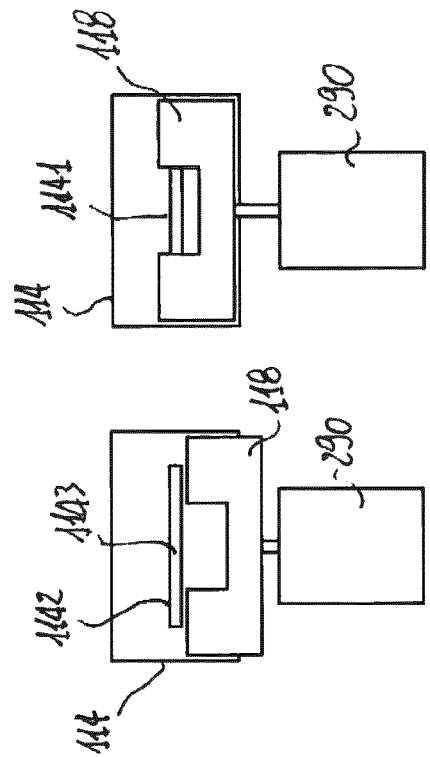
FIG. 9
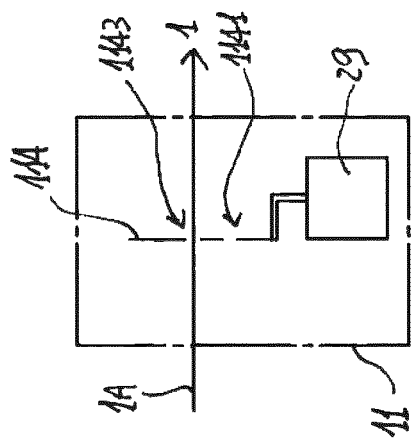
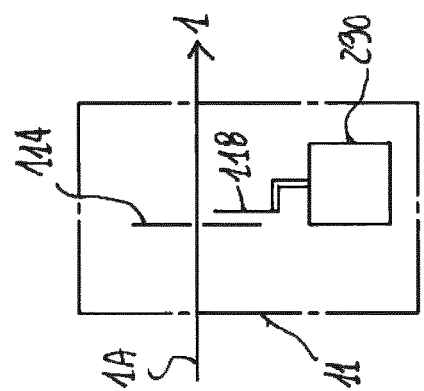

EYE FUNDUS INSPECTION APPARATUS

The present invention relates to an eye fundus inspection apparatus.

The apparatus according to the invention is particularly suitable for use in ophthalmology, when it is necessary to acquire images of the retina of the eye.

The use of eye fundus inspection apparatus adapted to acquire images of the retina is widely known.

Among these, eye fundus inspection apparatus of confocal type are also known.

For reasons of constructional simplicity, eye fundus inspection apparatus of confocal type of the type with line scanning, in particular those that use LED light sources, are of particular industrial and commercial interest.

Examples of these eye fundus inspection apparatus of confocal type with line scanning are described in the patent documents U.S. Pat. Nos. 7,331,669, 7,831,106B2, US20140232987A1, WO2016/037980A1 and US20160227998A1.

Inspection apparatus of this type are arranged to scan the retina with a light beam that illuminates a linear shaped retinal region.

In these apparatus, the light reflected by the retina is collected and passed through a confocal diaphragm provided with a suitably shaped confocal opening (for example slit shaped) to reduce the amount of parasitic light coming from unwanted reflections.

The reflected light beam, passing through the confocal diaphragm, is received by an acquisition sensor adapted to acquire images of the retina.

In some construction designs, these apparatus can use one or more LEDs as light sources. In these cases, considering the limited level of radiance of the LEDs, it is not possible to project a light output sufficient to acquire images of the retina, if the illuminated retinal region is very narrow.

Consequently, the light beam that illuminates the retina is typically shaped so that the retinal region illuminated has a linear shape of relatively high width, for example comprised between $1/100$ and $1/5$ of its length.

This means that the confocal diaphragm also has a confocal opening of relatively high width, with approximately the same ratio between width and length.

The relatively high width of the opening of the confocal diaphragm reduces its capacity to efficiently filter the unwanted parasitic light coming from zones other than the retina, in particular the scattered light from the crystalline lens, particularly intense in the case in which the eye examined is affected by cataract.

The parasitic light coming from the crystalline lens gives rise to marked "blurring" effects that can make the images acquired useless for medical diagnosis.

A particular type of confocal eye fundus inspection apparatus with line scanning comprises apparatus destined to provide fluorescence images of the retina.

These inspection apparatus illuminate the retina with an excitation light having wavelength typically in the blue or green region. They comprise, besides the components described above, filter means capable of blocking the reflected excitation light and allowing fluorescence light, emitted by particular fluorescent substances present on the retina and having higher wavelengths with respect to the wavelengths of the illumination light, to pass towards the sensor.

As is known, in the case of acquisition of fluorescence images of the retina, the crystalline lens of the eye absorbs a part of the excitation light and emits fluorescence light that overlaps the fluorescence light emitted by the retina, thereby reducing the contrast of the images acquired by the acquisition sensor (presence of "blurring" effects).

To reduce the influence of parasitic light coming from the crystalline lens on the images of the retina, some prior art apparatus, for example those described in the patent documents cited above, are provided with light beam separating means (for example a separation diaphragm) destined to create, at the level of the crystalline lens, an optical separation between the illumination light beam and the light beam reflected by the retina. Separation of the beams at the level of the crystalline lens reduces the blurring effects in the images acquired by the sensor, but without reducing them sufficiently.

The solutions proposed in the patent documents cited do not provide practical solutions that satisfactorily reduce the parasitic light scattered by the crystalline lens or emitted, by fluorescence, therefrom.

The patent document WO20170049323A1 describes a solution for improving the level of contrast in the images of the retina (whether coloured or fluorescence) acquired.

In the apparatus described in this patent document, an illumination light beam is scanned along the retina with a movement in subsequent steps, according to a scanning direction.

At a series of discrete positions, separate from one another, the light beam illuminates different retinal regions having linear shape with relatively high width.

A light beam reflected by the retina is passed through a confocal diaphragm and directed towards an acquisition sensor that acquires a plurality of partial images of the retina, each of which shows a retinal region illuminated with the light beam positioned in a corresponding discrete position.

The retinal region shown in each of these images has a length approximately equal to the length of the region illuminated by the light beam and a width wider than the width of the region illuminated by the light beam.

Each partial retinal image shows a plurality of parallel regions of the retina having a same length, side by side along their longer side and arranged in succession according to the scanning direction of the light beam.

These parallel regions comprise, in succession according to the scanning direction, a first "dark" zone, a first slightly brighter transition zone, a brighter central zone and a second "dark" zone.

Each region has a linear shape oriented according to a direction perpendicular to the scanning direction.

The partial images of the retina, thus acquired, are combined to reconstruct an overall retinal image.

The patent document mentioned above also describes a processing procedure of the images which provides for:
  processing the partial images of the retina, described above, to acquire data indicative of the light level of the "dark" zones present in the aforesaid images;
  correcting the overall retinal image based on the data thus acquired to reduce the "blurring" effects caused by the presence of parasitic light.

The solution illustrated above has some drawbacks.

Firstly, it is not very efficient for obtaining a satisfactory reduction of the parasitic light scattered or emitted, through fluorescence, by the crystalline lens.

Another drawback consists in the need to acquire a large number of partial images of the retina to reconstruct an overall image. This requires the provision of relatively complex and costly data processing means in order to obtain an overall retinal image without inconvenient delays for the user. Moreover, there is a high probability of the overall retinal image thus reconstructed having reconstruction artifacts.

A further drawback consists in the fact of requiring complicated and costly scanning means of the light beam, which can move the light beam with rapid controlled movements so that each of the partial images of the retina is acquired with the light beam stopped in one of the discrete positions mentioned above to prevent or reduce the presence of motion artifacts in the images acquired.

A further drawback consists in the fact that the acquisition time to acquire an overall retinal image is relatively long. Therefore, there is a high probability of the overall retinal image acquired being affected by motion artifacts of the eye.

The main aim of the present invention is to provide an eye fundus inspection apparatus, of confocal line scanning type, which solves the aforesaid problems of prior art.

Within this aim, an object of the present invention is to provide an eye fundus inspection apparatus capable of producing colour or fluorescence images of the retina, which have a high level of contrast, also in cases in which the eye being examined is affected by cataract or other disorders.

A further object of the present invention is to provide an eye fundus inspection apparatus capable of producing wide field images of the retina, which have a high degree of contrast, also in cases in which the eye being examined is affected by cataract or other disorders.

A further object of the present invention is to provide an eye fundus inspection apparatus capable of performing quantitative measurements of fluorescence of the retina.

A further object of the present invention is to provide an eye fundus inspection apparatus that is easy to produce on an industrial scale, at competitive costs.

This aim and these objects, together with other objects that will be more apparent from the subsequent description and from the accompanying drawings, are achieved according to the invention by an eye fundus inspection apparatus according to claim 1 and to the related dependent claims, proposed hereunder.

Figure 16:
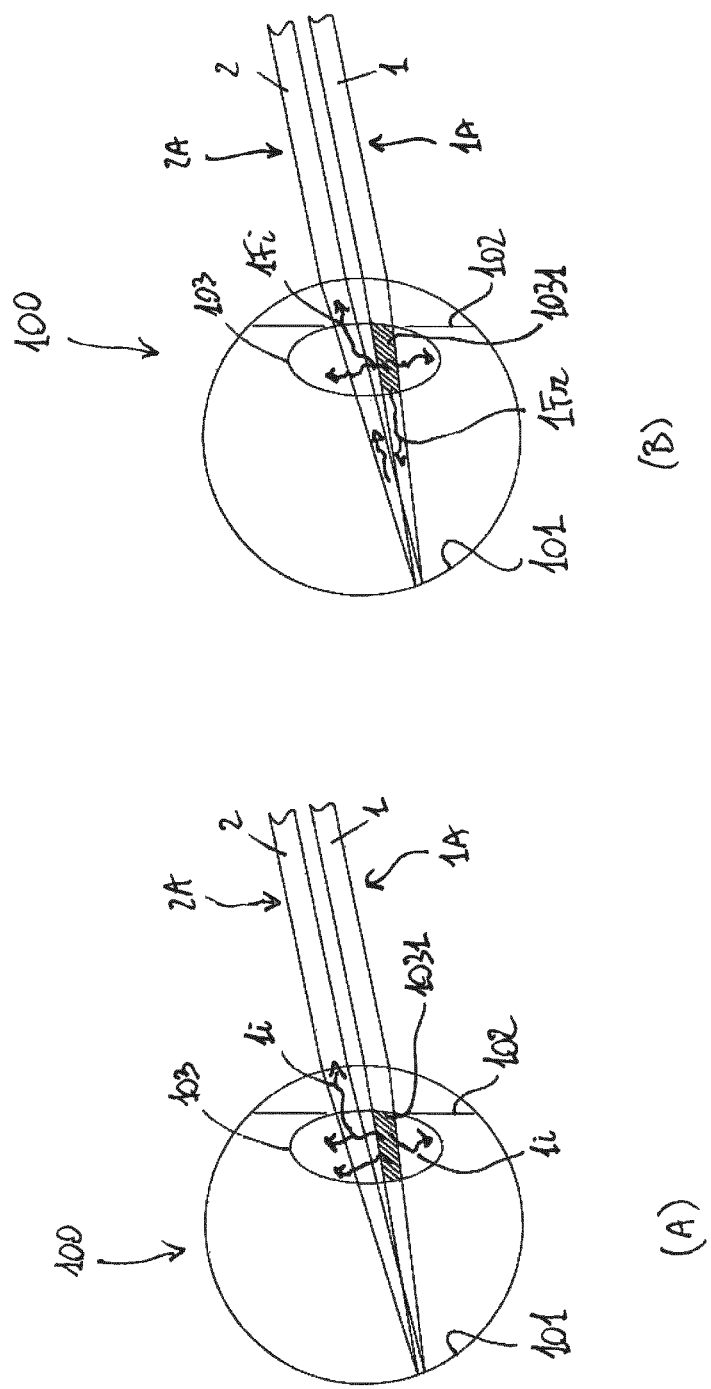

Characteristics and advantages of the eye fundus inspection apparatus according to the invention will be more apparent with reference to the description given below and to the accompanying figures, provided purely for explanatory and non-limiting purposes, wherein:

FIGS. 1, 2, 3, 4 and 5 schematically illustrate some embodiments of the eye fundus inspection apparatus according to the invention;

FIGS. 6, 7, 8, 9 and 10 schematically illustrate some embodiments of subsystems forming the eye fundus inspection apparatus according to the invention;

FIGS. 11, 12, 13, 14 and 15 schematically illustrate operation of the eye fundus inspection apparatus according to the invention;

FIG. 16 schematically illustrates the scattering and generation of parasitic light inside the crystalline lens of the eye, when an illumination light beam passes through it.

The present invention relates to an eye fundus inspection apparatus 500, in particular of the confocal type with line scanning.

In a general definition thereof, the apparatus 500 comprises:
  illumination means 12 comprising at least a light source and adapted to project a first light beam 1 to illuminate a retina 101 of an eye 100;
  an optical lighting path 1A for the first light beam 1;
  acquisition means 27 adapted to receive a second light beam 2 coming at least partially from the retina;
  an optical acquisition path 2A for the second light beam 2;
  scanning means 17 adapted to move the first light beam 1 on the retina.

Figure 12:
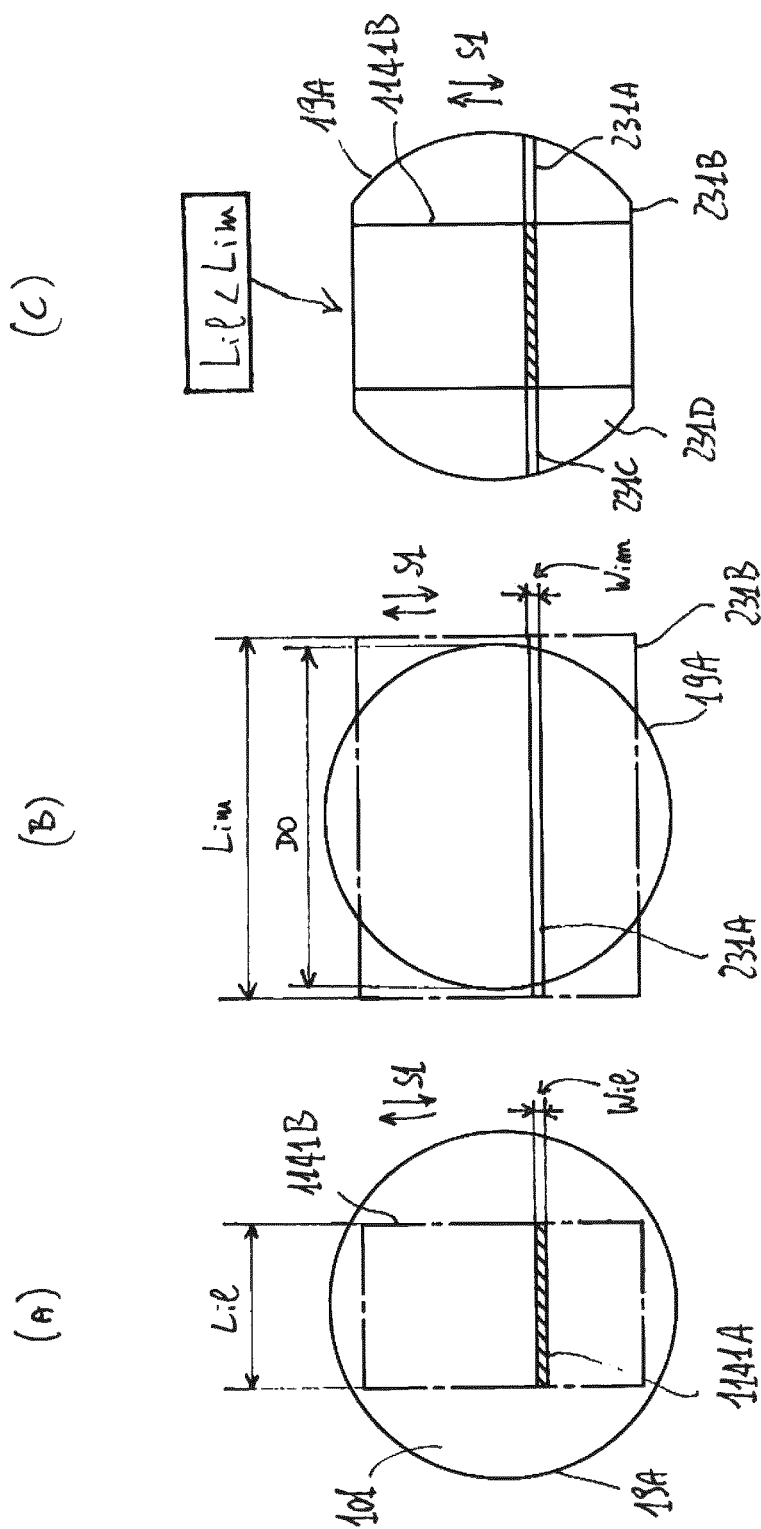

The scanning means 17 can perform a linear scan, i.e., move the light beam 1 with a linear movement, according to a first rectilinear scanning direction S1. In this way, the light beam 1, moving with respect to the retina according to the scanning direction S1, travels over and illuminates a retinal area having a substantially rectangular shape (FIG. 12).

Figure 13:
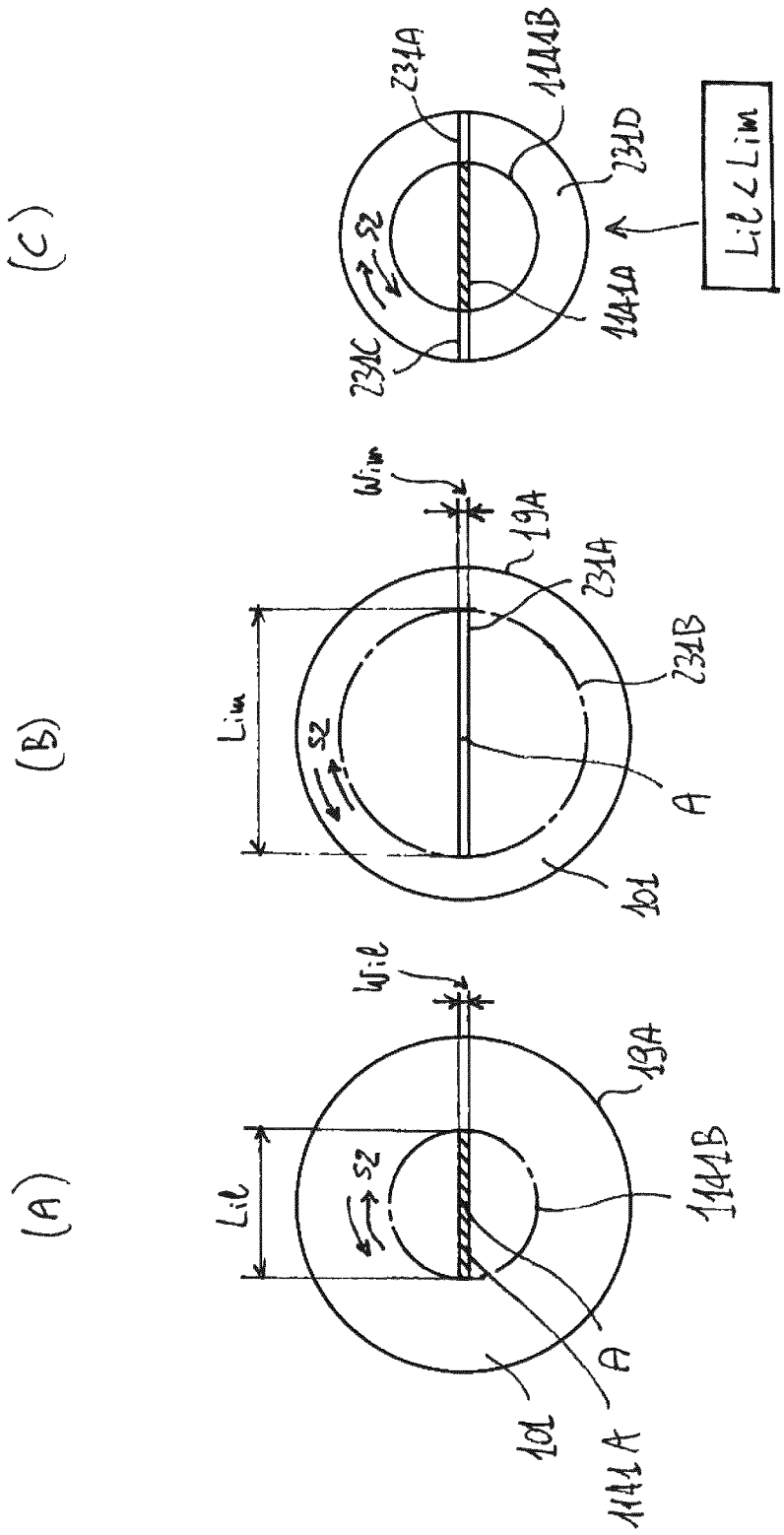

Alternatively, the scanning means 17 can perform a circular scan, i.e., move the light beam 1 with respect to the retina with a rotational movement about a rotation axis A, according to a circular scanning direction S2. In this way, the light beam 1, moving with respect to the retina according to the scanning direction S2, travels across and illuminates an area of retina having a substantially circular shape (FIG. 13).

The apparatus 500 further comprises:
  light beam separating means 16 adapted to define, at the level of the pupil 102 of the eye, separate passage zones for the first light beam 1 and for the second light beam 2;
  a control unit 120 adapted to control operation of the inspection apparatus. This control unit advantageously comprises data processing means adapted to provide images of the retina;
  first shaping means 11 of the light beams adapted to provide a first passage section 1141 for the first light beam 1. The first passage section 1141 is arranged in a position optically conjugated with the retina and defines, on the retina, a light projection region 1141A at which the first light beam 1 is projected on the retina 101. The light projection region 1141A has a linear shape with a length Lil, measured along a direction perpendicular to the first scanning direction S1, or in radial direction with respect to the second scanning direction S2, and a width Wil, measured along a direction parallel to the first scanning direction S1 or tangential with respect to the second scanning direction S2;
  second light beam shaping means 23, 271, 272 adapted to provide a second passage section 2310 for the second light beam 2. The second passage section 2310 is arranged in a position optically conjugated with the retina and defines, on the retina, a light acquisition region 231A from which the second light beam 2 comes at least partially. The light acquisition region 231A has a linear shape with a length Lim, measured along a direction perpendicular to said first scanning direction S1 or radial with respect to the second scanning direction S2, and a width Wim, measured along a direction parallel to the first scanning direction S1 or tangential with respect to the second scanning direction S2.

For greater clarity of exposition, it is specified that, within the scope of the present invention, the definition "optically conjugated" identifies positioning in the exact position of optical conjugation or in a relatively small neighbourhood (with respect to the lengths of the optical paths of the apparatus 500) of the exact position of optical conjugation.

With reference to FIG. 1, there is now described a first embodiment of the invention.

In this embodiment, the apparatus comprises illumination means 12 provided with at least a light source and adapted to project a first light beam 1 on the retina.

The apparatus 500 comprises a first optical lighting path 1A for the first light beam 1.

Preferably, the illumination means 12 comprise a light source 121, preferably of LED type.

In use of the apparatus 500, the light beam 1 passes along the optical path 1A towards the retina 101.

Figure 6:
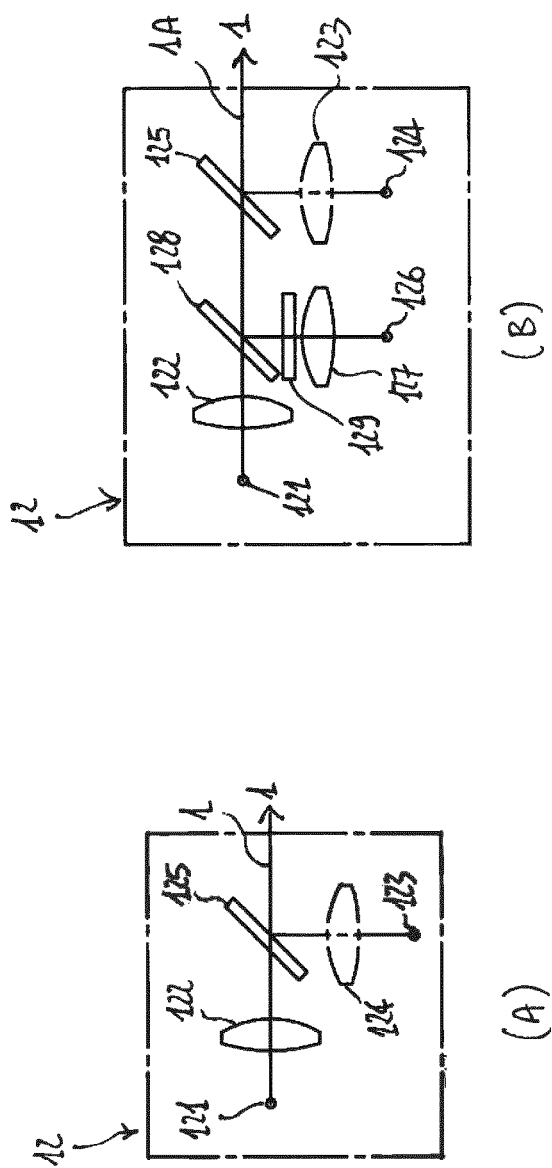

In the variant of embodiment shown in FIG. 6-(A), illumination means 12 comprise, in addition to the light source 121, at least another light source 123, optically coupled to the lighting path 1A by means of at least a dichroic mirror 125.

In this case, the illumination means 12 can advantageously be arranged to provide a light suitable for the acquisition of various types of photos of the retina, for example infrared light or white light. The light generated by the sources 121, 123 is preferably collimated by means of the collimation lenses 122, 124.

In the embodiment shown in FIG. 6-(B), illumination means 12 comprise at least a light source 126 capable of emitting an excitation light suitable to excite the fluorescent substances of the retina.

If necessary, the light generated by the light source 126 can be collimated through the collimation lens 127 and filtered by second filter means 129 to select a given bandwidth of wavelengths from the light emitted by the source 126.

Preferably, illumination means 12 also comprise the aforementioned light sources 121, 123. In this case, the various light sources are coupled to the optical path 1A directly or by means of dichroic mirrors 128, 125.

The constructional solution shown in FIG. 6-(B) allows the apparatus 500 to produce images using light reflected by the retina 101, as well as fluorescence images of the retina, as will be illustrated in more detail below.

The apparatus 500 further comprises first shaping means 11 adapted to define a section of linear shape for the light beam 1.

Figure 7:
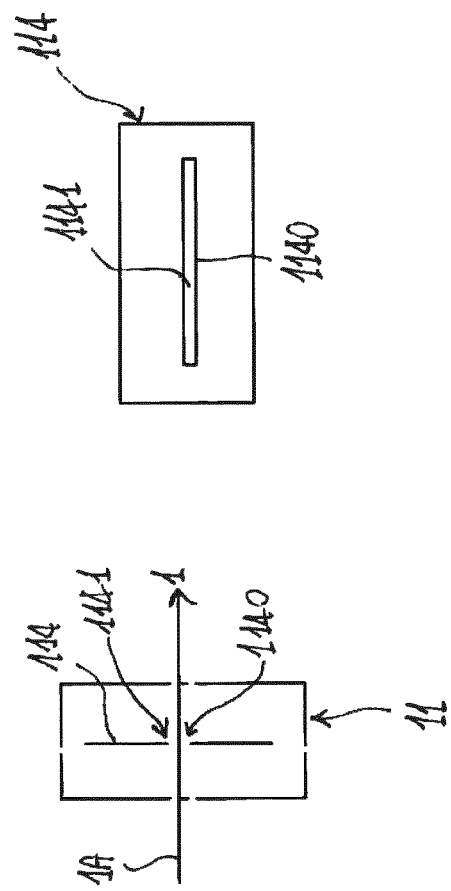

With reference to FIGS. 7, 8 and 9, these show some variants of embodiment of the first shaping means 11 of the light beam 1.

In the variant of embodiment shown in FIG. 7, the first shaping means 11 comprise a projection diaphragm 114 arranged to be optically conjugated with the retina 101.

The projection diaphragm 114 advantageously comprises at least a first projection opening 1140 that defines a first passage section 1141 for the light beam 1 projected by the light source 121.

Figure 11:
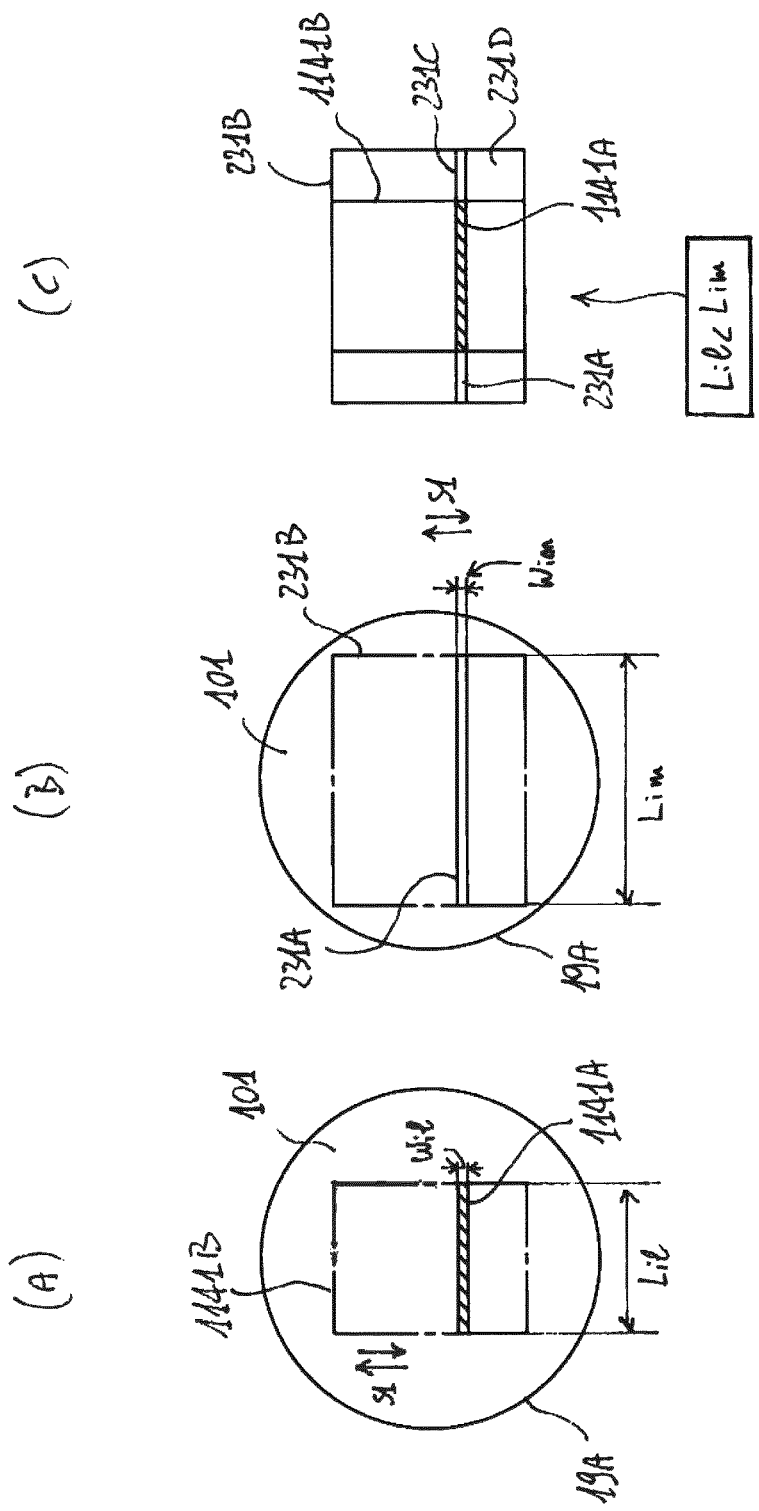

The first passage section 1141 for the light beam 1 is optically conjugated with the retina and defines on the retina a linear shaped light projection region 1141A (FIG. 11).

The light projection region 1141A has a length Lil measured along a direction perpendicular to the first scanning direction S1 and a length Wil measured along a direction parallel to the first scanning direction S1 (linear scanning).

Moreover, the light projection region 1141A preferably has a length Lil much larger than its width Wil. For example, the ratio between the sizes Wil/Lil can vary from ⅕ to ¹⁄₁₀₀.

According to the variants of embodiment shown in the FIGS. 8 and 9, the projection diaphragm 114 of the first shaping means 11 is adjusted to provide differentiated projection openings 1140, 1142 for the light beam 1.

The projection openings 1140, 1142 have an elongated shape and are arranged to define passage sections 1141, 1143 of different length for the light beam 1.

Figure 15:
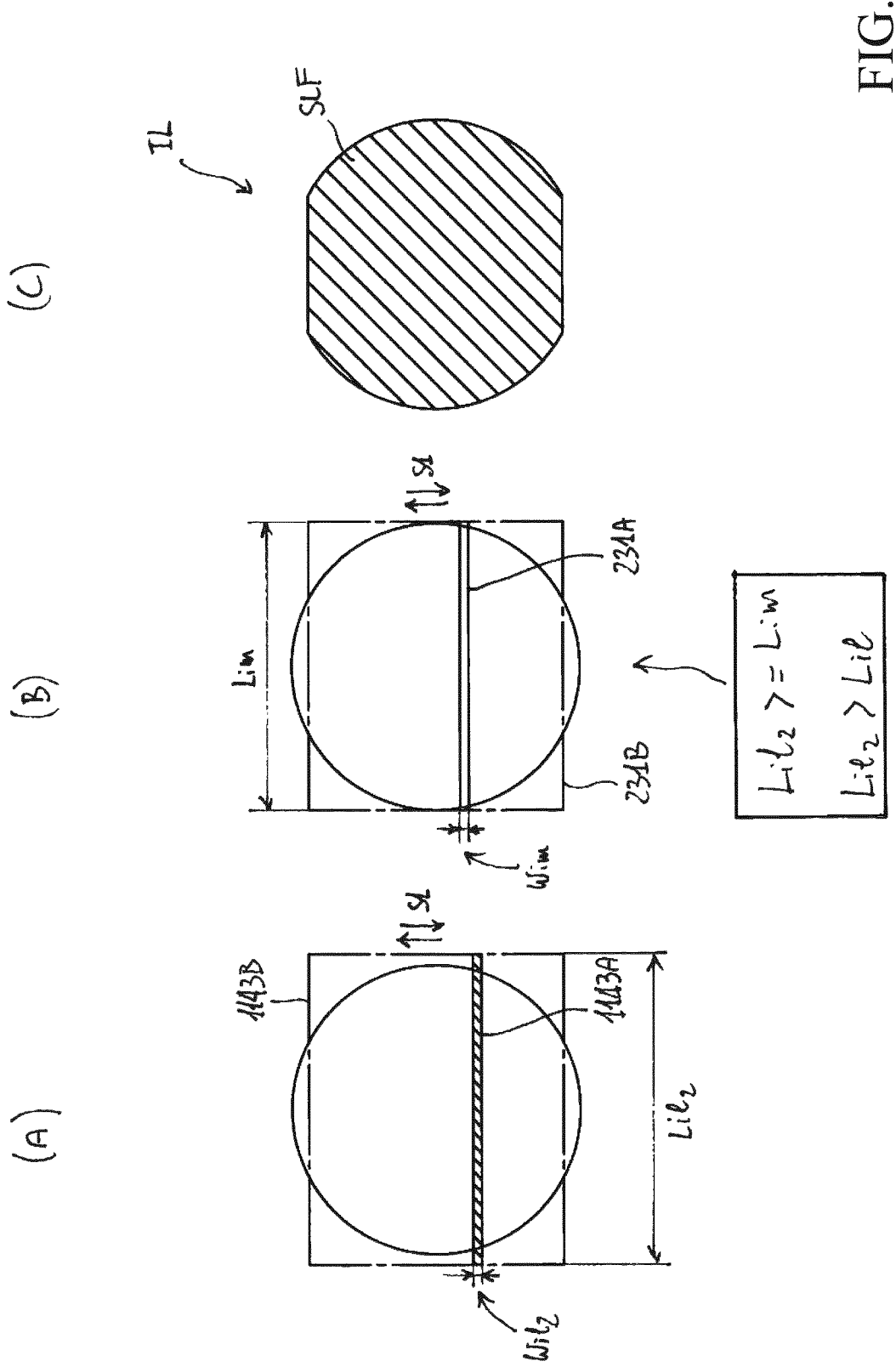

These passage sections, optically conjugated with the retina, define light projection regions 1141A, 1143A of different length on the retina 101 (FIGS. 11 and 15).

In general, the light projection regions 1141A, 1143A both have a linear shape.

The light projection region 1141A has a length Lil and width Wil measured as described for the variant of embodiment of FIG. 7.

The light projection region 1143A has a length $Lil_2$ measured along a direction perpendicular to the first scanning direction S1 and a length $Wil_2$ measured along a direction parallel to the first scanning direction S1 (linear scanning).

Moreover, the light projection region 1143A preferably has a length $Lil_2$ much longer than its width $Wil_2$. For example, the ratio between the sizes Wil/Lil can vary from ⅕ to ¹⁄₁₀₀.

According to the variants of embodiment of FIGS. 8 and 9, the passage section 1141 has a length shorter than the passage section 1143 and defines, on the retina 101, a light projection region 1141A having a length Lil shorter than the length $Lil_2$ of the light projection region 1143A defined by the passage section 1143.

In the variant of embodiment of FIG. 8, the projection diaphragm 114 comprises a first projection opening 1140 adapted to define a first passage section 1141 for the light beam 1, having a shorter length, and a second projection opening 1142 adapted to define a third passage section 1143 for the light beam 1, having a longer length.

Advantageously, the projection diaphragm 114 is reversibly movable in a first coupling position with the optical lighting path 1A, at which the first projection opening 1140 is optically coupled with the optical lighting path 1A, and in a second coupling position with the optical lighting path 1A, at which the second projection opening 1142 is optically coupled with the optical lighting path 2A.

Preferably, the projection diaphragm 114 is moved by actuator means 29.

From the above, it is evident that, by moving the projection diaphragm 114 between the two coupling positions described, it is possible to selectively vary the length of the retinal region illuminated by the light beam 1, given that different passage sections 1141, 1143 define light projection regions 1141A, 1143A of different length on the retina 101.

In the variant of embodiment of FIG. 9, the projection diaphragm 114 comprises a second projection opening 1142 arranged to define a third passage section 1143 for the light beam 1, having a longer length.

The projection diaphragm 114 is operatively coupled with a mask 118 reversibly movable in a first masking position and in a second masking position.

Preferably, the mask 118 is moved by actuation means 290.

At the first masking position, the mask 118 does not cover the second projection opening 1142.

At the second masking position, the mask 118 partially covers the second projection opening 1142 to obtain a projection opening corresponding to the first projection opening 1140.

From the above, it is evident that, by moving the mask 118 between the two masking positions described, it is possible to selectively vary the length of the retinal region illuminated by the light beam 1, given that each position of the mask 118 corresponds to a different passage section for the light beam 1.

The different passage sections 1140, 1143, thus obtained, define, on the retina 101, light projection regions 1141A, 1143A having differentiated length Lil, $Lil_2$, respectively a shorter length Lil and a larger length $Lil_2$.

Other constructional solutions are possible for the first shaping means 11 of the beam, evident for those skilled in the art.

For example, in a further constructional solution, not illustrated, the first shaping means of the beam can comprise a long and narrow mirror arranged in a position conjugated with the retina 101 and which defines by reflection the linear section of the light beam 1. In this case, the passage section 1141 for the light beam 1 is formed by the surface of this mirror.

The apparatus 500 comprises acquisition means 27 adapted to receive a second light beam 2 coming from the retina 101 to allow the acquisition of one or more images of the retina by the control unit 120.

The apparatus 500 comprises an optical acquisition path (or imaging optical path) 2A for the second light beam 2.

In use of the apparatus 500, the light beam 2, starting from the retina 101, passes along the optical acquisition path 2A until reaching the acquisition means 27.

The acquisition means 27 comprise at least a sensor capable of receiving the light beam 2 at a receiving surface optically conjugated with the retina 101.

In the embodiment of FIG. 1, the acquisition means 27 can comprise a two-dimensional sensor of CCD or C-MOS type.

The apparatus 500 comprises first scanning means 17 adapted to perform a linear scan, i.e., to move the light beam 1 projected on the surface of the retina 101 according to the first a scanning direction S1.

Advantageously, the first scanning means 17 also have the function of de-scanning the light beam 2 and directing it along the optical acquisition path 2A towards the acquisition means 27.

For the scanning means 17, various constructional solutions are possible, for example using oscillating mirrors moved by galvanometers or resonance mechanisms, polygonal mirrors, micromirror arrays or the like.

According to the embodiment of FIG. 1, the apparatus 500 comprises second shaping means of the beam 2 arranged along the optical acquisition path 2A, in a position optically conjugated with the retina.

In the embodiment of FIG. 1, the second shaping means comprise a confocal diaphragm 23.

The confocal diaphragm 23 preferably comprises at least a confocal opening 231 (of elongated shape) that defines a second passage section 2310 for the light beam 2 directed towards the acquisition means 27. This passage section is optically conjugated with the retina and defines a corresponding light acquisition region 231A on the retina 101 (FIG. 11).

The light acquisition region 231A has a linear shape with a length Lim measured along a direction perpendicular to the first scanning direction S1 and a width Wim, measured along a direction parallel to the first scanning direction S1.

According to the embodiment of FIG. 1, the apparatus 500 comprises second scanning means 171 adapted to scan the light beam 2 on the receiving surface of the acquisition means 27.

Preferably, the second scanning means 171 have a movement synchronous with the first scanning means 17.

Preferably, the first scanning means 17 and the second scanning means 171 can be produced as a single assembly, for example using a resonant oscillating mirror with two mutually opposite reflecting surfaces.

According to the embodiment of FIG. 1, the apparatus 500 comprises light beam separating means 16 adapted to separate the light beam 1 from the light beam 2 at the pupil 102 of the eye 100.

The light beam separating means can, for example, comprise at least a separation diaphragm of the light beams.

Due to the light beam separation means 16, the light beam 2 passes through a predetermined zone of the pupil 102 separated from the zone of pupil through which the light beam 1 enters the eye.

Preferably, the apparatus 500 comprises a first lens 15 arranged along the optical lighting path 1A between the beam shaping means 11 and the light beam separation means 16.

Preferably, the apparatus 500 comprises an eyepiece 19, arranged along the optical lighting path 1A, between the first scanning means 17 and the eye 100.

If necessary, the apparatus 500 can also comprise a scanning lens 18 arranged between the first scanning means 17 and the eyepiece 19.

Preferably, the apparatus 500 also comprises a second lens 21, a third lens 25, an objective 26 arranged along the optical path 2A, between the beam separation means 16 and the acquisition means 27.

The apparatus 1 advantageously comprises a control unit 120 adapted to control its operation.

Advantageously, the control unit 120 comprises data processing means (for example a microprocessor) capable of executing software instructions to perform the functions required.

Advantageously, the control unit 120 is adapted to execute one or more data processing procedures to process the information acquired by the acquisition means 27.

Based on the information acquired by the acquisition means 27, the control unit 120 is capable of acquiring and/or processing images of the retina and generating control signals to control operation of some components of the apparatus 500, for example the illumination means 12, the acquisition means 27 and any actuator means comprised in the apparatus 500.

Preferably, the control unit 120 also comprises user interface means (not illustrated), for example a monitor, a keyboard and/or a mouse.

If necessary, the apparatus 500 can comprise first filter means 28 adapted to allow passage towards the acquisition means 27 of only a part of the light beam 2 having a predefined band of wavelengths.

Figure 10:
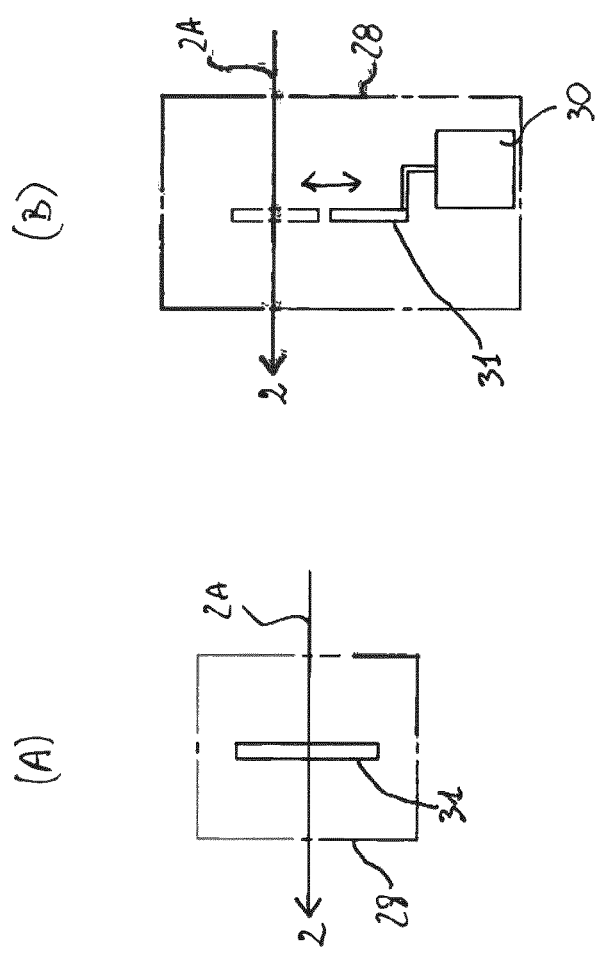

In a possible solution shown in FIG. 10-(A), the filter means 28 comprise a filter 31 inserted in the imaging path 2A.

In the solution shown in FIG. 10-(B), the filter means 28 are arranged to be able to be inserted in or removed from the acquisition path 2A. To this end, a filter 31 can be moved by an actuator 30, controlled by the control unit 120 by means of suitable control signals.

With the solution shown in FIG. 10-(B) it is possible to produce a multifunctional apparatus 500, capable of acquiring images obtained with light reflected by the retina as well as fluorescence images of the retina, as will be explained below.

With reference to FIG. 1, the general operation of the apparatus 500 is now described in greater detail.

In use of the apparatus 500, the illumination means 12 provide the first light beam 1.

This latter is shaped by the shaping means 11 by passage through the passage section 1141.

Moreover, the light beam 1 passes through the lens 15 and the light beam separating means 16.

The light beam 1 is scanned by the scanning means 17 that direct it towards the retina 101.

The light beam 1 passes through the scanning lens 18 and the eyepiece 19 and enters the eye 100 to illuminate the retina 101.

On the retina 101, the light beam 1 illuminates a light projection region 1141A that moves along the retina, according to a first scanning direction S1 (linear scanning) imposed by the scanning means 17, traveling across a first retinal area 1141B.

The light projection region 1141A has a linear shape with a length Lil measured along a direction perpendicular to the first scanning direction S1 and a width Wil measured along a direction parallel to the first scanning direction S1 (FIG. 11).

Preferably, the light projection region 1141A has a length Lil much longer than its width Wil. For example, the ratio between the sizes Wil/Lil can vary from ⅕ to ¹⁄₁₀₀.

Illumination of the retina 101 by the light beam 1 causes the formation of a light beam 2 exiting from the retina 101.

In particular, the light beam 2 can be formed by light reflected or emitted, by fluorescence (natural or induced), from the retina at a light acquisition region 231A that moves along the retina synchronously with the light projection region 1141A, according to the scanning direction S1 imposed by the scanning means 17, traveling across a second retinal area 231B (FIG. 11).

The light acquisition region 231A has a linear shape with a length Lim measured along a direction perpendicular to the first scanning direction S1 and a width Wim measured along a direction parallel to the first scanning direction S1.

Preferably, the light acquisition region 231A has a length Lim much longer than its width Wim. For example, the ratio between the sizes Wim/Lim can vary from ⅕ to ¹⁄₁₀₀.

The light beam 2 from the retina 101 exits from the eye through the pupil 102, at a separate zone from the zone through which the light beam 1 passes, and passes back through the eyepiece 19 and the scanning lens 18.

The scanning means 17 descan the light beam 2 transforming it into a fixed beam and simultaneously directing it along the optical path 2A, towards the light beam separating means 16.

The light beam 2 then passes through the lens 21, if necessary is filtered by the filter means 28, passes through the confocal opening 231 of the confocal diaphragm 23, which is fixed, passes through the lens 25.

The second scanning means 171 scan the light beam 2 again, simultaneously directing it along the optical path 2A towards the acquisition means 27.

The light beam 2 passes through the lens 26 and reaches the receiving surface of the acquisition means 27 that transmit information to the control unit 120 to acquire one or more images of the retina 101.

Figure 2:
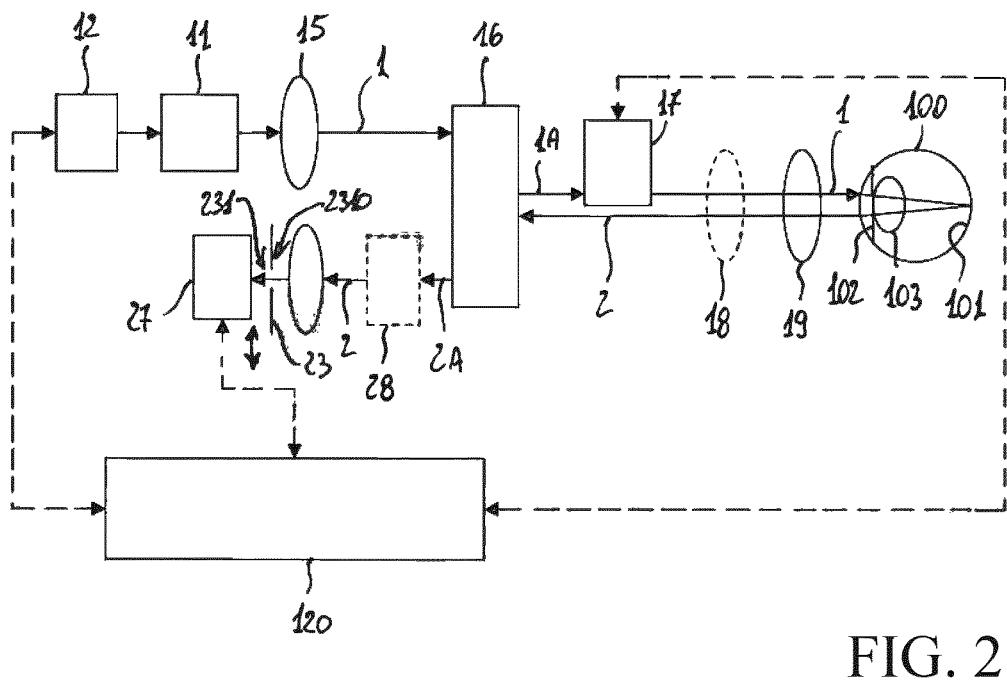

A further embodiment of the apparatus 500 is shown in FIG. 2.

This embodiment has a structure and operation similar, in many aspects, to the embodiment of FIG. 1.

Unlike this latter, the first scanning means 17 do not perform descanning of the beam 2 but are simply arranged to direct the light beam 2 towards the beam separating means and subsequently along the optical acquisition path 2A.

The second scanning means 171 are absent in this embodiment of the invention.

In the embodiment of FIG. 2 of the apparatus 500, the first shaping means 11 of the light beam 1 are identical to the first shaping means already described in relation to FIGS. 1, 7, 8 and 9. They comprise a projection diaphragm 114 or other shaping means adapted to define a passage section 1141 identical to that of the embodiment of FIG. 1 described above.

In the embodiment of FIG. 2 of the apparatus 500, the second shaping means of the light beam 2 comprise a confocal diaphragm 23 identical to the one described for the embodiment of FIG. 1 described above.

However, in this case the confocal diaphragm 23 is produced so that it can move synchronously with the movement of the scanning means 17.

Figure 3:
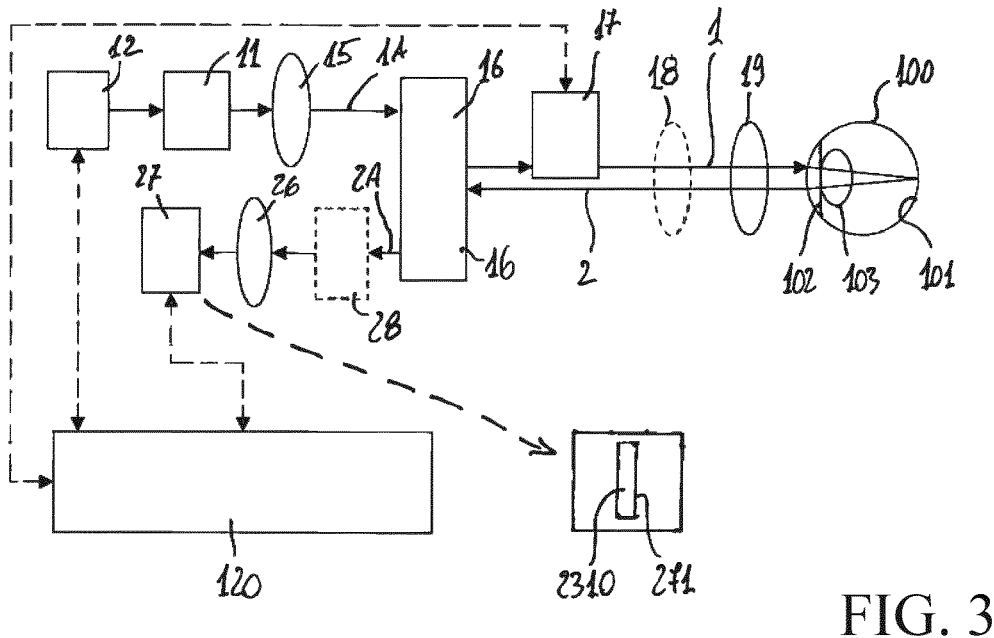

A further embodiment of the apparatus 500 is shown in FIG. 3.

This embodiment has a structure and operation similar, in many aspects, to the embodiment of FIG. 2.

However, unlike this latter, in the embodiment of FIG. 3, the receiving surface of the acquisition means 27 (for example a sensor of C-MOS type with "rolling shutter" operation) comprises receiving surface portions 271 that can be selectively activated to receive the light beam 2.

The receiving surface portions 271 can be selectively activated (by sending suitable control signals) by the control unit 120 through a mobile electronic windowing process of the pixels present in the receiving surface of the acquisition means 27.

Each surface portion 271, when selectively activated by the control unit 120, defines a first passage section 2310 for the light beam 2. This passage section is optically conjugated with the retina and defines a corresponding light acquisition region 231A on the retina 101.

In practice, each surface portion 271, when selectively activated, ha similar functions to those of the confocal opening 231 of the mobile confocal diaphragm 23 described in relation to FIG. 2.

Therefore, in the embodiment of FIG. 3, the apparatus 500 does not comprise the confocal diaphragm 23. Moreover, the scanning means 17 do not perform descanning of the light beam 2 but are simply arranged to direct the light beam 2 along the optical acquisition path 2A.

Advantageously, the control unit 120 selectively activates the various surface portions 271 of the receiving surface of the acquisition means 27 synchronously with the movement of the scanning means 17.

In the embodiment of FIG. 3 of the apparatus 500, the first shaping means 11 of the light beam 1 are identical to the first shaping means already described in relation to FIGS. 1, 7, 8 and 9. They comprise a projection diaphragm 114 or other shaping means adapted to define a passage section 1141 identical to that of the embodiment of FIG. 1 described above.

Instead, the second shaping means comprise the active portion 271 of the receiving surface of the acquisition means 27 that defines the passage section 2310.

Figure 4:
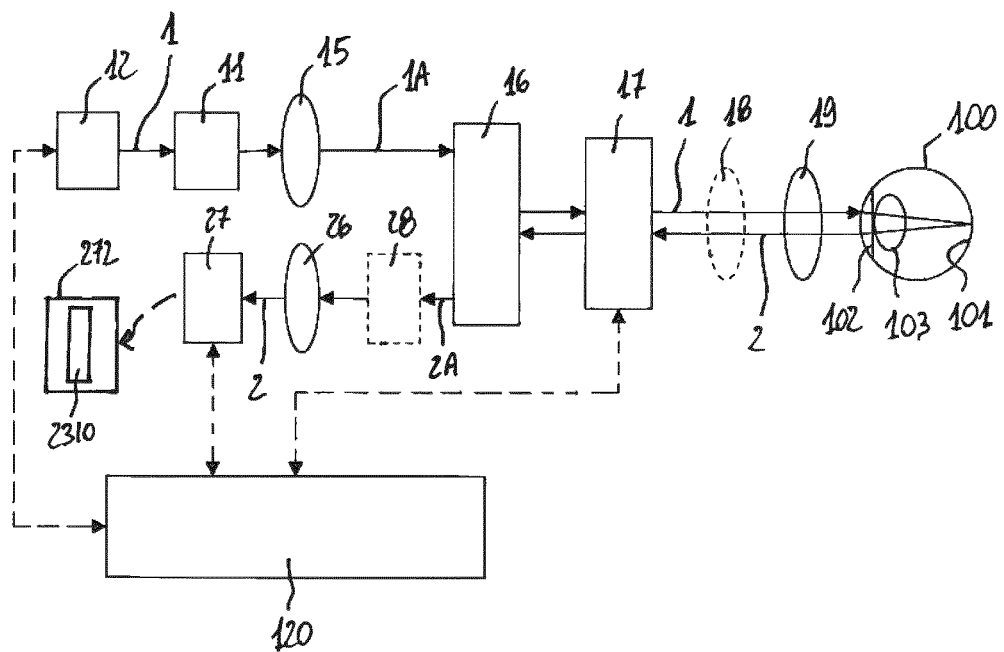

A further embodiment of the apparatus 500 is shown in FIG. 4.

This embodiment has a structure and operation similar, in many aspects, to the embodiment of FIG. 3.

Unlike this latter, in the embodiment of FIG. 4 the light beam 2 coming from the retina is descanned by the scanning means 17 and directed towards the acquisition means 27 that comprise a TDI sensor having at least a sensitive surface portion 272 formed by pixels arranged in a matrix on a long and narrow rectangular area.

The sensitive surface portion 272 of the TDI sensor (or the whole sensitive surface of this latter) can be activated by sending suitable control signals by the control unit 120 and defines a second passage section 2310 for the light beam 2.

This passage section is optically conjugated with the retina and defines a corresponding light acquisition region 231A on the retina 101.

In practice, the sensitive surface portion 272 of the TDI sensor (or the whole sensitive surface of this latter) has similar functions to those of the confocal opening 231 of the confocal diaphragm 23 described above.

Therefore, in the embodiment of FIG. 4, the apparatus 500 does not comprise the confocal diaphragm 23.

In the embodiment of FIG. 4 of the apparatus 500, the first shaping means 11 of the light beam 1 are identical to the first shaping means already described in relation to FIGS. 1, 7, 8 and 9. They comprise a projection diaphragm 114 or other shaping means adapted to define a passage section 1141 identical to that of the embodiment of FIG. 1 described above.

Instead, the second shaping means comprise the sensitive surface portion 272 of the TDI sensor (or the whole sensitive surface of this latter) that defines the passage section 2310.

Figure 5:
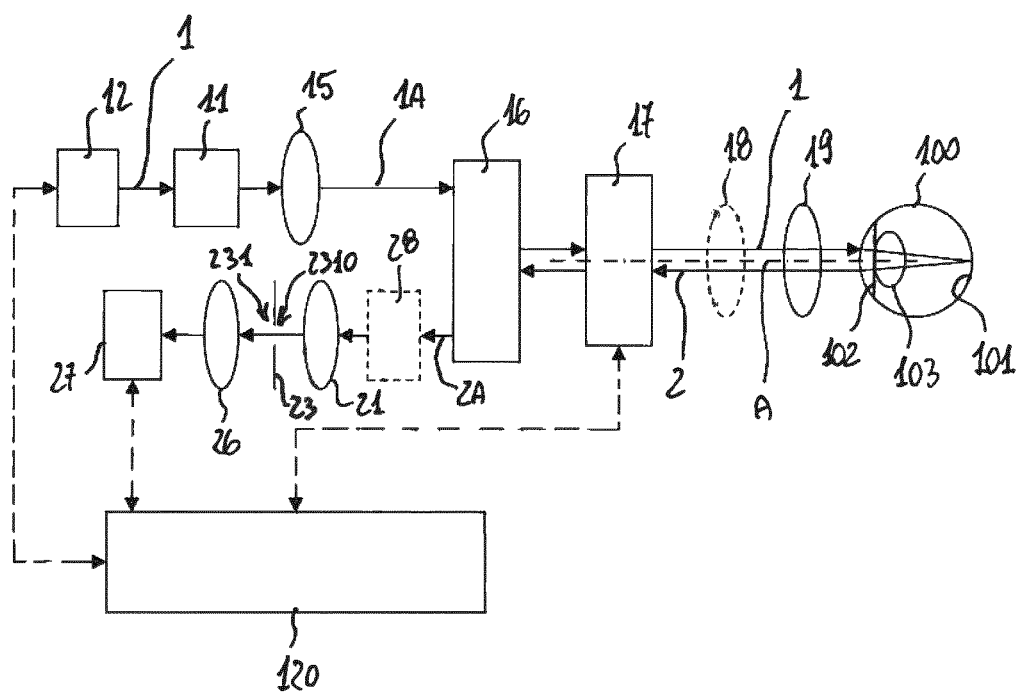

A further embodiment of the apparatus 500 is shown in FIG. 5.

This embodiment has a structure and operation similar, in many aspects, to the embodiment of FIG. 1.

However, unlike this latter, in the embodiment of FIG. 5, the first scanning means 17 are adapted to perform circular scanning of the light beam 1, i.e., move the light beam 1 projected on the surface of the retina 101 about the rotation axis A, according to the circular second scanning direction S2.

In the embodiment of FIG. 5 of the apparatus 500, the first shaping means 11 of the light beam 1 are identical to the first shaping means already described in relation to FIGS. 1, 7, 8 and 9. They comprise a projection diaphragm 114 or other shaping means adapted to define a passage section 1141 identical to that of the embodiment of FIG. 1 described above.

The passage section 1141 defines a projection region 1141A having a linear shape with a length Lil measured along a direction radial with respect to the second scanning direction S2 and a length Wil measured along a direction tangential with respect to the second scanning direction S2 (FIG. 13).

Moreover, the light projection region 1141A preferably has a length Lil much longer than its width Wil. For example, the ratio between the sizes Wil/Lil can vary from $1/5$ to $1/100$.

On the retina 101, the light beam 1 illuminates a light projection region 1141A that moves along the retina according to the second scanning direction S2 imposed by the scanning means 17, traveling over a first retinal area 1141B.

The same scanning means 17 are adapted to descan the light beam 2 coming from the retina transforming it into a fixed beam.

Moreover, the light beam 2 passes through the confocal diaphragm 23 and is received by the acquisition means 27.

The confocal diaphragm 23 preferably comprises at least a confocal opening 231 (of elongated shape) that defines a second passage section 2310 for the light beam 2 directed towards the acquisition means 27. This passage section is optically conjugated with the retina and defines a corresponding light acquisition region 231A on the retina 101.

The light acquisition region 231A has a linear shape with a length Lim measured along a direction radial with respect to the second scanning direction S2 and a width Wim, measured along a direction tangential with respect to the second scanning direction S2 (FIG. 13).

Further solutions (not illustrated) to perform circular scanning are possible.

For example, the first scanning means 17 can be produced as a group of two separate assemblies that perform synchronous rotation movements, one of which rotates the light beam 1 while the other rotates the confocal diaphragm 23.

Besides the solution that uses a confocal diaphragm 23, other solutions, applicable in the case of an apparatus 500 that performs circular scanning, are possible.

According to an example, similar to the one shown in relation to FIG. 3, the acquisition means 27 can comprise a receiving surface having surface portions 271 that can be selectively activated to receive the light beam 2.

According to a further example, similar to the one shown in relation to FIG. 4, the acquisition means 27 can comprise a TDI sensor having at least a sensitive surface portion 272. The sensitive surface portion 272 or the whole surface of the sensor TDI define the passage section 2310.

Those skilled in the art will understand that further embodiments of the apparatus 500 directly derivable from the embodiments described above, are possible.

For example, it is possible to produce equipment intended for the acquisition of fluorescence images of the retina by suitably combining the configurations illustrated in the FIGS. 1 to 9.

Moreover, in an apparatus 500 produced according to one of the embodiments illustrated in FIGS. 1-5, it is possible to use on the lighting path 1A illumination means 12 containing at least a light source 126 capable of emitting an excitation light suitable to excite fluorescent substances of the retina, if necessary together with the filter means 129, while the filter means 28 described above are used on the imaging path 2A of the same apparatus.

According to the invention, the above described first shaping means 114 and second shaping means 23, 271, 272 of the light beams are arranged so that (FIGS. 11 and 13):
  the light projection region 1141A and the light acquisition region 231A are at least partially mutually overlapped;
  the light projection region 1141A has a length Lil shorter than the length Lim of the light acquisition region 231A.

Preferably, the projection opening 1140 for the light beam 1 and the confocal opening 231 (FIG. 1, 2, 5) or 271 (FIG. 3) or 272 (FIG. 4) for the light beam 2, respectively produced by the first and second shaping means described above, are advantageously shaped to define respective passage sections 1141, 2310 for the light beams 1, 2 having the following characteristics:
  the passage sections 1141, 2310 have an elongated shape (for example rectangular or with variable width) and extend along a corresponding main longitudinal axis;
  the positions of the passage sections 1141 and 2310, together with the lenses of the optical lighting path 1A and the lenses of the optical acquisition path 2A are arranged so that the conjugates on the retina of the passage sections 1141 and 2310, i.e., the light projection region 1141A and the light acquisition region 231A, are oriented in directions parallel to each other.

In FIG. 11, for an apparatus 500 having scanning means 17 arranged to perform a linear scan of the light beam 1, the light projection region 1141A and the light acquisition region 231A, viewed according to a plane parallel to the first scanning direction S1 (practically, as defined on the retina) are shown separately (references (A)-(B)) and overlapped (reference (C)).

It can be noted how, at the surface of the retina, the light projection region 1141A, illuminated by the light beam 1, has a length Lil shorter than the length Lim of the light acquisition region 231A, from which the light beam 2 comes at least partially.

Due to the action of the scanning means 17, the light projection region 1141A and the light acquisition region 231A move synchronously along the retina, constantly remaining overlapped.

During the synchronous movement of the light projection region 1141A and of the light acquisition region 231A along the retina, the light projection region 1141A travels over a first retinal area 1141B (FIG. 11-(A)) while the light acquisition region 231A travels over a second retinal area 231B (FIG. 11-(B)).

As can be seen from FIG. 11-(C), the second retinal area 231B is larger with respect to the first retinal area 1141B and differs from this latter by one or more third retinal areas 231D.

Having a longer length Lim and partially overlapping the light projection region 1141A, the light acquisition region 231A comprises one or more non-overlapping portions 231C. These non-overlapping portions, during the synchronous movement of the light projection region 1141A and of the light acquisition region 231A along the retina, travel over the third retinal areas 231D.

Advantageously, when the light projection region 1141A and the light acquisition region 231A are centred with respect to each other, the third retinal areas 231C extend beyond the ends of the projection region 1141A.

In the example shown in FIG. 11, the light projection region 1141A and the light acquisition region 231A have lengths Lil, Lim shorter than the diameter of the available optical field 19A (i.e., of the maximum retinal section that can be observed). This latter is defined by the lenses of the apparatus 500, in particular by the eyepiece 19.

In this case, both retinal areas 1141B, 231B travelled by the light projection region 1141A and by the light acquisition region 231A can be observed by the acquisition means 27.

This solution, although allowing correct acquisition of the images of the retina, does not allow the available optical field to be fully exploited.

In the example shown in FIG. 12, the light projection region 1141A and the light acquisition region 231A have lengths Lil, Lim respectively shorter and longer than the diameter DO of the available optical field 19A (FIG. 12-(A)-(B)).

In this case, the retinal area 231B travelled by the light acquisition region 231A cannot be observed completely by the acquisition means 27 but is limited by the (curved) edges of the available optical field 19A (FIG. 12-(C)).

Nonetheless, this solution allows correct acquisition of the images of the retina and, simultaneously, allows the available optical field to be exploited to a greater extent.

In FIG. 13, for an apparatus 500 having scanning means 17 arranged to perform a circular scan of the light beam 1, the light projection region 1141A and the light acquisition region 231A are shown separately (references (A)-(B)) and overlapped (reference (C)).

The light projection region 1141 and the light acquisition region 231A are viewed along the rotation axis A of the scanning means 17 (practically, as defined on the retina).

It can be noted how at the surface of the retina the light projection region 1141A, illuminated by the light beam 1, has a length Lil shorter than the length Lim of the light acquisition region 231A, from which the light beam 2 comes at least partially.

Due to the action of the scanning means 17, the light projection region 1141A and the light acquisition region 231A perform a rotational movement about the axis A, synchronously (with the movement of the first light beam 1 imposed by the scanning means 17) remaining constantly overlapped.

During the rotational movement of the light projection region 1141A and of the light acquisition region 231A about the axis A, the light projection region 1141A travels over a first retinal area 1141B (FIG. 13-(A)) while the light acquisition region 231A travels over a second retinal area 231B (FIG. 13-(B)).

As can be observed from the figure (FIG. 13-(C)), the second retinal area 231B is larger with respect to the first retinal area 1141B and differs from this latter by one or more third retinal areas 231D.

Having a longer length Lim and being partially superimposed on the light projection region 1141A, the light acquisition region 231A comprises one or more non-overlapping portions 231C. These non-overlapping portions, during the synchronous rotation movement of the light projection region 1141A and of the light acquisition region 231A along the retina, travel over the third retinal areas 231D.

Advantageously, when the light projection region 1141A and the light acquisition region 231A are centred with respect to each other, the third retinal areas 231D form an annulus centred in the rotation axis A.

Figure 14:
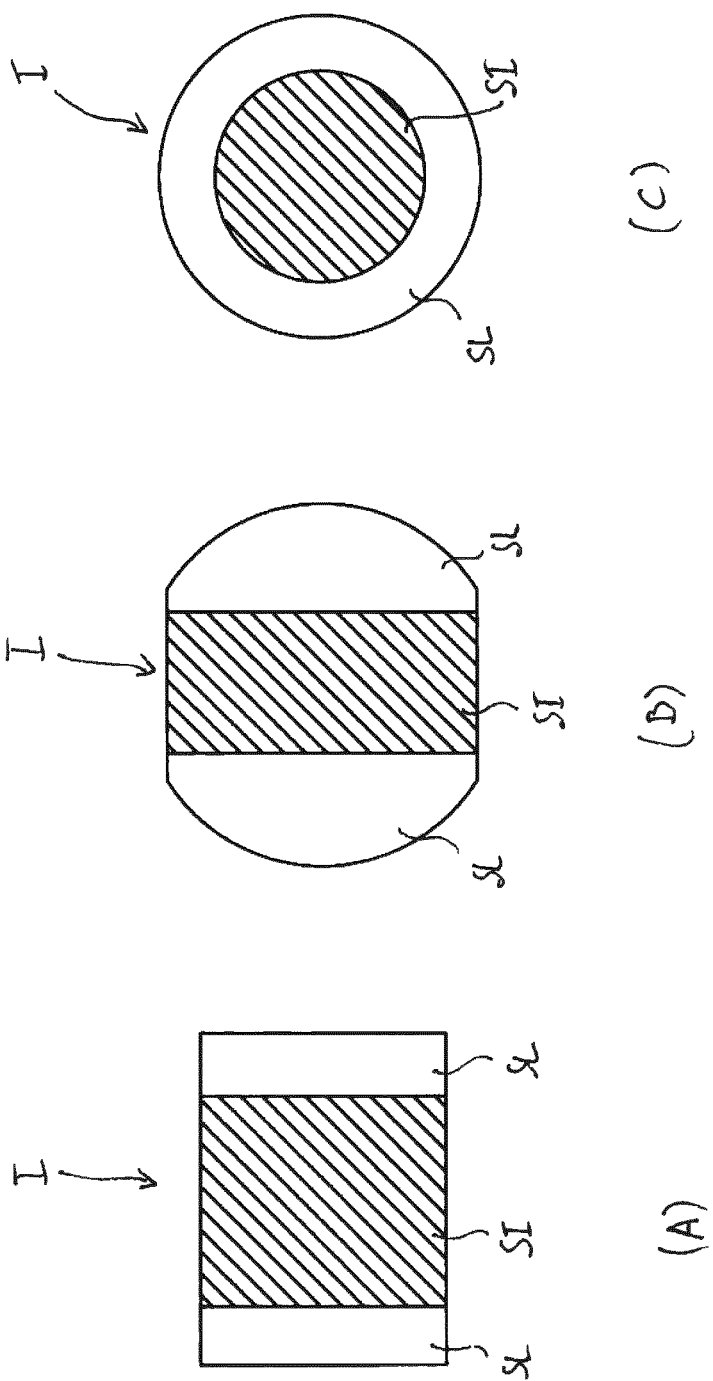

With reference to FIG. 14, this shows an image I (of reflected or fluorescence light) of the retina acquired by the acquisition means 27 when the light projection region 1141A, illuminated by the light beam 1, has a length Lil shorter than the length Lim of the light acquisition region 231A, from which the light beam 2 comes (at least partially).

FIGS. 14(A) and 14(B) show examples of images I in an apparatus 500 having scanning means 17 arranged to perform a linear scan of the light beam 1 (FIGS. 1-4 and 11-12).

The image I comprises a first light zone SI corresponding to the first illuminated retinal area 1141B, travelled by the light projection region 1141A during the synchronous linear movement of the light projection region 1141A and of the light acquisition region 231A along the retina.

FIG. 14(C) shows an image I acquired in an apparatus 500 having scanning means 17 arranged to perform a circular scan of the light beam 1 (FIGS. 5 and 13).

Also in this case, the image I comprises a first light zone SI corresponding to the first illuminated retinal area 1141B, travelled by the light projection region 1141A during the synchronous circular movement of the light projection region 1141A and of the light acquisition region 231A about the axis A.

In both cases, the image I comprises one or more second light zones SL, corresponding to the third retinal areas 231C travelled by the non-overlapping portions 231C between the light acquisition region 231A and the light projection region 1141A during their synchronous movement on the retina (linear or circular).

The examples of FIGS. 14(A) and 14(B) are particular cases in which there are several light zones SL. These cases correspond to an apparatus 500 having scanning means 17 arranged to perform a linear scan of the first light beam 1 and for which the light acquisition region 231A and the light projection region 1141A of the retina are centred with each other. As can be seen, the image I comprises at the centre the first light zone SI and, at the edges of this latter, the second light zones SL.

The example of FIG. 14(C) represents a particular case of an apparatus 500 having scanning means 17 arranged to perform a circular scan of the first light beam 1 and for which the light acquisition region 231A and the light projection region 1141A of the retina are both centred with the axis A. As can be observed, the image I comprises at the centre the first light zone SI, in the shape of a disc and, around this, a second light zone SL, in the shape of an annulus.

As illustrated above, the first light zone SI represents, in practice, the image on the surface of the acquisition means of the retinal area illuminated by the light beam 1 during the scanning movement of this latter on the surface of the retina. Consequently, light coming from the retina and parasitic light, mixed together, can simultaneously reach the zone SI.

The zones SL represent retinal areas that are not illuminated by the light beam 1. Consequently, parasitic light can substantially reach the zones SL.

In use of the apparatus 500 for the acquisition of images obtained with light reflected by the retina (for example colour images of the retina), this parasitic light is formed of light scattered or reflected from zones of the eye or of the apparatus 500 that are not conjugated with the retina 101, in particular, as known, from the crystalline lens of the eye 103, especially if affected by cataract.

Part of this parasitic light enters the acquisition path 2A and is captured by the acquisition means 27 as a distribution of light that overlaps the retinal image.

If coming from zones of the eye or of the apparatus very close to the "scanning pivot" of the light beam 1 (which is normally close to the pupil and to its optical conjugates), this parasitic light determines a substantially homogeneous distribution of light that overlaps the retinal image.

If coming from zones of the eye or of the apparatus farther from the "scanning pivot" of the light beam 1, the aforesaid parasitic light determines an uneven distribution of light that overlaps the retinal image.

In any case, in a retinal image, the presence of this parasitic light overlapping the retinal image determines a reduction of the contrast of this latter ("blurring effects").

The parasitic light generated through scattering within the crystalline lens overlaps the retinal image more or less homogeneously given that it comes from a zone of the optical path close to the scanning pivot.

FIG. 16-(A) shows the effect of scattering of the light within the crystalline lens in the case of acquisition of a retinal image obtained with light reflected by the retina.

The light 1*i*, scattered in the passage zone 1031 of the beam 1 in the crystalline lens 103, bounces inside the crystalline lens making it bright.

Part of this parasitic light 1*i* scattered within the crystalline lens enters the acquisition path 2A, passes through the confocal opening 231 and is more or less homogeneously distributed on both the zones 1141B and 231D of the retina, therefore overlapping the image I of the retina acquired, in particular at the zones SI and SL of this latter.

In fact, this parasitic light is added to the light coming from the zones 1141B and 231D of the retina and is therefore present in the zones SI and SL of the image I.

The more or less homogeneous distribution on the zones SI and SL of the image I of the scattered light within the crystalline lens is justified by the fact that the crystalline lens zone that scatters this parasitic light is very close to the small and almost fixed zone (scanning pivot) through which all the rays that form the light beam 2 that creates the whole image I pass.

Therefore, the brightness contribution provided by the parasitic light scattered within the crystalline lens on the zones SI and SL is more or less the same and is measurable at the second light zones SL of the image I taken by the acquisition means 27.

This information can be used to subtract the contribution of the parasitic light from the zone SI of the retinal image and obtain a retinal image less disturbed by parasitic light.

In use of the apparatus 500 for the acquisition of fluorescence images of the retina, this parasitic light is formed by fluorescence light emitted from zones of the eye that are not conjugated with the retina 101, in particular, as known, from the crystalline lens of the eye 103, especially if affected by cataract.

In fact, in the case of capturing a fluorescence retinal image, the parasitic light must have wavelengths corresponding to the bandwidth of the filter means 28 to be capable of passing towards the acquisition means 27 and blurring the fluorescence retinal image.

Therefore, in this case, the parasitic light is not produced by a scattering or reflection of the light beam 1 (whose wavelength does not allow passage through the filter means 28), but is produced through fluorescence, above all within the crystalline lens and in particular if this latter is affected by cataract.

As known, the crystalline lens of the eye 103 absorbs blue light and generates green fluorescence light. The fluorescence of the crystalline lens is particularly strong in the case of eyes with cataract.

FIG. 16-(B) shows two components of the fluorescence light generated by the crystalline lens. The component 1Fi of the fluorescence light generated in the passage zone 1031 of the beam 1 through the crystalline lens represents the portion of fluorescence light of the crystalline lens that is scattered within the crystalline lens, making it bright.

Part of the fluorescence light scattered within the crystalline lens manages to directly enter the acquisition path 2A, passes through the filter 31 and the confocal opening 231 and overlaps the fluorescence retinal image acquired.

The fluorescence light 1Fi scattered within the crystalline lens comes from a small and almost fixed zone (close to the scanning pivot). Therefore, it causes a more or less homogeneous increase of the fluorescence brightness in the fluorescence retinal image acquired.

Another portion of the fluorescence light generated in the passage zone 1031 of the light beam 1 through the crystalline lens is the component 1Fr directed towards the retina.

This fluorescence light (green), generated by the crystalline lens, illuminates the retina more or less homogeneously and is subsequently reflected by this latter. The part of the light 1Fr reflected by the retina in the overlapped zone between the lighting path and the acquisition path partially enters the acquisition path 2A overlapping the fluorescence light produced by the retina. The fluorescence light 1Fr, reflected by the retina, passes through the filter 31 and the confocal opening 231 and more or less homogeneously increases the brightness of the fluorescence retinal image acquired.

The parasitic fluorescence light produced by the components 1Fi and 1Fr of the fluorescence light of the crystalline lens causes a decrease in the contrast of the final fluorescence retinal image.

As illustrated above, part of this parasitic fluorescence light passes (within the crystalline lens) through the acquisition path 2A and is captured by the acquisition means 27 as a more or less homogeneous distribution of fluorescence light that overlaps the retinal image.

In a fluorescence retinal image, the presence of this parasitic light overlapping the retinal image determines a reduction of the contrast of this image ("blurring effects").

Given that it comes from a zone of the optical path close to the scanning pivot, the parasitic fluorescence light generated by the fluorescence of the crystalline lens, overlaps on the fluorescence retinal image more or less homogeneously.

Therefore, the brightness contribution provided by this parasitic fluorescence light generated by the crystalline lens on the zones SI and SL is more or less the same and is measurable at the second light zones SL of the image acquired.

This information can be used to subtract the contribution of parasitic light from the zone SI of the fluorescence retinal image and obtain a fluorescence retinal image less disturbed by parasitic light.

According to some embodiments of the invention (shown in one of FIGS. 1 to 5 together with one of FIG. 8 or 9), the first light beam shaping means 11 are adapted to provide also a third passage section 1143 for the first light beam 1, which is shaped to define a light projection region 1143A having a length $Lil_2$ longer than or equal to the length Lim of the light acquisition region 231A (FIG. 15).

In the variant of embodiment of the first shaping means 11 of FIG. 8, the projection opening 1142 of the movable projection diaphragm 114 can advantageously be shaped to define a third passage section 1143 shaped to define, when coupled with the optical lighting path 1A, with the projection diaphragm 114 positioned in the second coupling position, a light projection region 1143A having a length $Lil_2$ longer than or equal to the length Lim of the light acquisition region 231A.

In the variant of embodiment of the first shaping means 11 of FIG. 8, the projection opening 1142 of the projection diaphragm 114 can advantageously be shaped to define a third passage section 1143 that defines, when coupled with the optical lighting path 1A, without being partially covered by the mask 118, a light projection region 1143A having a length $Lil_2$ longer than or equal to the length Lim of the light acquisition region 231A.

When the first light beam shaping means 114 comprise a third passage section 1143 of the type illustrated above, the light acquisition region 231A travels, along the retina, a second retinal area 231B completely within the first illuminated retinal area 1141B, travelled by the light projection region 1141A (FIGS. 15-(A) and 15-(B)).

With reference to FIG. 15(C), this shows an image I of the retina (also called "wide field retinal image") acquired by the acquisition means 27 when the light projection region 1141A, illuminated by the light beam 1, has a length longer than or equal to the length Lim of the light acquisition region 231A, from which the light beam 2 comes at least partially.

The image I comprises a single third light zone SLF corresponding to the retinal area 1141B, 231A travelled by the light projection region 1141A during the synchronous movement of the light projection region 1141A and of the light acquisition region 231A along the retina.

Due to the first and second light beam shaping means, advantageously arranged as illustrated above, the control unit 120 (more in particular the related data processing means) is capable of executing some processing procedures of the images acquired by the acquisition means 27 to obtain images with light reflected by the retina (for example colour images) or improved fluorescence retinal images, in particular with regard to their level of contrast.

In general, to execute these processing procedures, the control unit 120 is configured to:

acquire a retinal image obtained with light reflected by the retina or a fluorescence retinal image with the first and second shaping means arranged so that the light projection region 1141A, illuminated by the light beam 1, has a length Lil shorter than the length Lim of the light acquisition region 231A, from which the light beam 2 comes. As illustrated above, in this image, it is possible to observe a first light zone SI and one or more second light zones SL.

acquire detection data indicative of the light level of the second light zones SL of the retinal image obtained with light reflected by the retina or fluorescence retinal image;

process said retinal image obtained with light reflected by the retina or fluorescence retinal image based on the aforesaid detection data to obtain a further retinal image obtained with light reflected by the retina or a further fluorescence retinal image improved with respect to the image acquired directly.

For reasons of clarity it is specified that, in general, "retinal image obtained with light reflected by the retina" means a retinal image obtained without the filter 31 being in the acquisition path 2A. The light reflected by the retina is thus capable of reaching the sensor means 27 regardless of its wavelength. Examples of images from this category are colour images, infrared images and red-free images.

Some examples of embodiments of the apparatus 500 that illustrate some image processing procedures executable by the control unit 120 are now described.

First Image Processing Procedure

In a possible example of embodiment, the control unit 120 is configured to execute a first image processing procedure with which it is possible to obtain images obtained with light reflected by the retina improved with respect to the images that can be acquired directly by the acquisition means 27.

The aforesaid first processing procedure comprises a step of acquiring an image obtained with light reflected by the retina (for example a colour image).

Advantageously, this retinal image obtained with light reflected by the retina is acquired by the control unit 120 based on the information provided by the acquisition means 27.

For this acquisition, the first and second shaping means are arranged so that the light projection region 1141A, illuminated by the light beam 1, has a length Lil shorter than the length Lim of the light acquisition region 231A, from which the light beam 2 comes at least partially.

Moreover, a light source 121, 123, 124, 126 adapted to provide the type of light desired is appropriately activated and the filter 31, if provided, is decoupled from the optical acquisition path 2A.

As illustrated above, the retinal image obtained with light reflected by the retina acquired by the control unit 120 has a first light zone SI, having greater brightness, and one or more second light zones SL having reduced brightness (FIG. 14).

The aforesaid first processing procedure comprises a step of processing the retinal image obtained with light reflected by the retina, thus acquired, to obtain first detection data indicative of the fluorescence light level of said second light zones SL.

As illustrated above, the brightness of the second light zones SL is due to the light scattered or reflected from zones of the eye or of the apparatus 500 that are not conjugated with the retina 101, in particular, as is known, from the crystalline lens of the eye 103, especially if affected by cataract.

The first detection data thus obtained are therefore indicative of the light level of the parasitic light present in the retinal image obtained with light reflected by the retina, as acquired.

Preferably, the aforesaid first detection data are obtained by measuring in several points the light level at these second zones SL.

The aforesaid first processing procedure comprises a step of processing the retinal image obtained with light reflected by the retina, as acquired, and the first detection data to obtain a further retinal image obtained with light reflected by the retina.

In the case in which the retinal image originally acquired has a homogeneous distribution of parasitic light at the second zones SL (parasitic light source close to the "scanning pivot"), the further retinal image obtained with light reflected by the retina can be easily reconstructed based on the aforesaid first detection data.

In the case in which the retinal image originally acquired has a non-homogeneous distribution of parasitic light (parasitic light source at a distance from the "scanning pivot"), at the second zones SL, the further retinal image obtained with light reflected by the retina can be obtained by processing the aforesaid detection values based on an appropriate interpolation algorithm, which can be of known type.

Preferably, the processing step executed by the control unit 120 to provide the further retinal image obtained with light reflected by the retina comprises the construction, based on the aforesaid first detection data, of an image indicative of a distribution of parasitic light in the retinal image originally acquired.

The parasitic light retinal image can have a different extension with respect to the retinal image obtained with light reflected by the retina as acquired. For example, it can have an extension corresponding to the first light zone SI of the retinal image originally acquired.

Preferably, in this processing step the retinal image originally acquired is subtracted from the parasitic light retinal image, as constructed, to obtain a further retinal image obtained with light reflected by the retina that is less affected by the brightness contribution of the unwanted parasitic light.

The further retinal image obtained with light reflected by the retina thus has a reduction of the "blurring" effects caused by the parasitic light generated in zones of the apparatus 500 or of the eye 100 (in particular the crystalline lens) that are not conjugated with the retina 101.

This further retinal image obtained with light reflected by the retina has a higher contrast level, facilitating identification of any diseased retinal zones.

In a variant of embodiment thereof, in which the retina is illuminated activating a white light source and a retinal image obtained with light reflected by the retina (for example a colour image) is acquired, the aforesaid first processing procedure of the images comprises some steps to improve the tones of colour of the further retinal image obtained with light reflected by the retina, processed as illustrated above.

Preferably, the aforesaid first processing procedure of the images comprises:
  processing the aforesaid first detection data to obtain first estimation data indicative of the light absorption by the crystalline lens of the eye;
  adjusting one or more colour channels of the further retinal image obtained with light reflected by the retina based on said first estimation data.

As is widely known, the passage of light through the crystalline lens of the eye is also accompanied by selective absorption phenomena, the extent of which varies with the wavelength of the light that passes through the crystalline lens.

More precisely, the amount of light absorbed by the crystalline lens increases as the wavelength of the light that passes through the crystalline lens decreases.

Therefore, after having passed through the crystalline lens, the first light beam 1, intended to illuminate the retina, will have a spectrum with a blue component attenuated to a greater extent with respect to the green and red components.

For similar reasons, after having passed through the crystalline lens, the second light beam 2, coming from the retina, will have a spectrum with a blue component further attenuated with respect to the green and red components.

As is known, the amount of light absorbed by the crystalline lens increases with the opacity of this latter.

Consequently, the colour of a retinal image of an eye with crystalline lens affected by cataract will have a more orange colour tone (as a result of greater attenuation of the blue component) with respect to the colour retinal image of a healthy eye (which will have a pinker colour tone).

By appropriately processing (with algorithms that can be of known type) the first detection data indicative of the fluorescence light level of said second light zones SL of the retinal image obtained with light reflected by the retina, as acquired, it is possible to estimate the level of opacity of the crystalline lens and, consequently, obtain first estimation data indicative of its capacity of differentiated light absorption on the wavelength.

Based on the second estimation data indicative of the light absorption by the crystalline lens of the eye, it is possible to amplify the blue, green and red channels of the further retinal image processed with differentiated coefficients of amplification, calculated as a function of the aforesaid first estimation data.

In this way it is possible to at least partially offset the differentiated attenuation as a function of the wavelength of the light beams 1, 2 that pass through the crystalline lens.

The further retinal image, thus re-processed, has colours that better reflect the natural colours of the retina.

Second Image Processing Procedure

In a further example of embodiment, the control unit 120 is configured to execute a second image processing procedure that makes it possible to obtain improved fluorescence retinal images with respect to the fluorescence images acquired directly by the control unit 120.

The aforesaid second processing procedure comprises a step of acquiring a fluorescence retinal image.

Advantageously, this fluorescence retinal image is acquired by the control unit 120 based on the information provided by the acquisition means 27.

For this acquisition, the first and second shaping means are arranged so that the light projection region 1141A, illuminated by the light beam 1, has a length Lil shorter than the length Lim of the light acquisition region 231A from which the light beam 2 comes at least partially.

Moreover, a light source 126 capable of providing an appropriate excitation light capable of exciting the fluorescent substances present on the retina is appropriately activated and the filter 31 is advantageously coupled to the optical acquisition path 2A.

The fluorescence retinal image, thus acquired, has a first light zone SI, having greater brightness, and one or more second light zones SL having reduced brightness (FIG. 14).

The aforesaid second processing procedure comprises a step of processing the fluorescence retinal image, thus acquired, to obtain second detection data indicative of the fluorescence light level at the aforesaid second light zones SL.

As illustrated above, the fluorescence brightness of the second light zones SL is due to the fluorescence light emitted from zones of the eye that are not conjugated with the retina 101, in particular, as is known, from the crystalline lens of the eye 103, especially if affected by cataract.

The second detection data thus obtained are therefore indicative of the light level of the parasitic fluorescence light present in the fluorescence image, as acquired by the control unit 120.

Preferably, the aforesaid second detection data are obtained by measuring in several points the fluorescence light level at these second zones SL.

The aforesaid second processing procedure comprises a step of processing the fluorescence retinal image, as acquired, and the aforesaid second detection data to obtain a further fluorescence retinal image.

Preferably, this processing step comprises the construction, based on the aforesaid second detection data, of a fluorescence image indicative of a distribution of the parasitic fluorescence light in the fluorescence retinal image originally acquired.

This parasitic fluorescence light image can have a different extension with respect to the fluorescence image originally acquired by the control unit 120. For example, it can have an extension corresponding to the first light zone SI of the fluorescence retinal image originally acquired.

Preferably, in this processing step, the parasitic fluorescence light image, as constructed, is subtracted from the fluorescence retinal image, as acquired, to obtain a further fluorescence retinal image that is less disturbed by the brightness contribution of the parasitic fluorescence light.

The further fluorescence retinal image thus has a reduction of the "blurring" effects caused by the parasitic fluorescence light generated in zones of the eye 100 (in particular the crystalline lens) that are not conjugated with the retina 101.

This further fluorescence retinal image has greater contrast, facilitating identification of any diseased retinal zones.

In a variant of embodiment thereof, the second image processing procedure allows fluorescence images particularly useful to perform quantitative measurements of the fluorescence light emitted from the retina to be obtained.

Normally, these quantitative measurements of the fluorescence light are highly disturbed by the presence of the crystalline lens that:
- absorbs an unknown quantity of excitation light 1 before this reaches the retina;
- absorbs an unknown quantity of fluorescence light 2 during its passage through the crystalline lens;
- adds to the fluorescence retinal image an unknown quantity of parasitic light substantially generated through the fluorescence of the crystalline lens.

According to this variant of embodiment, the aforesaid second processing procedure comprises a step of receiving a retinal image obtained with light reflected by the retina.

Advantageously, this retinal image obtained with light reflected by the retina is acquired by the control unit 120 based on the information provided by the acquisition means 27.

For this acquisition, the first and second shaping means are arranged so that the light projection region 1141A, illuminated by the light beam 1, has a length Lil shorter than the length Lim of the light acquisition region 231A from which the light beam 2 comes.

A first preferred solution for acquiring the retinal image obtained with light reflected by the retina is to activate the excitation source 126 and acquire the retinal image, with the filter 31 decoupled from the acquisition path 2A.

A second preferred solution is to acquire a retinal image, activating a source (121, 123, 124) capable of projecting white light, with the filter 31 decoupled from the acquisition path 2A.

The aforesaid retinal image obtained with light reflected by the retina has a first light zone SI, having greater luminosity, and one or more second light zones SL, having reduced luminosity (FIG. 14).

The aforesaid second processing procedure comprises a step of processing said retinal image obtained with light reflected by the retina to obtain first detection data indicative of the fluorescence light level of said second light zones SL.

The first detection data, thus obtained, are indicative of the light level of the parasitic light present in the aforesaid retinal image obtained with light reflected by the retina, as acquired by the control unit 120.

Therefore, the aforesaid second processing procedure comprises the following steps:
- processing said first detection data to obtain second estimation data indicative of the level of opacity of the crystalline lens of the eye to excitation light;
- processing said second estimation data to obtain third estimation data indicative of a level of absorption of fluorescence light by the crystalline lens of the eye;
- adjusting the brightness of said further fluorescence retinal image based on said second estimation data and third estimation data.

By appropriately processing the first detection data indicative of the fluorescence light level of said second light zones SL of the aforesaid first retinal image obtained with light reflected by the retina, it is possible to estimate the level of opacity of the crystalline lens and, consequently, obtain second estimation data regarding the capacity of excitation light absorption (light beam 1) by the crystalline lens.

Based on the aforesaid second estimation data, indicative of the capacity of excitation light absorption by the crystalline lens, it is possible to adjust the brightness of the further fluorescence retinal image, as processed, to offset attenuation of the excitation light caused by the crystalline lens.

Instead, by appropriately processing the first detection data indicative of the fluorescence light level of said second light zones SL of the aforesaid first retinal image obtained with light reflected by the retina, it is possible to estimate the level of opacity of the crystalline lens and, consequently, obtain third estimation data regarding the capacity of fluorescence retinal light absorption (light beam 2) by the crystalline lens.

Based on the aforesaid third estimation data indicative of the capacity of fluorescence light absorption by the crystalline lens, it is possible to adjust the brightness of the further fluorescence retinal image, as processed, to offset the attenuation of fluorescence light 2 caused by the crystalline lens.

The further fluorescence retinal image thus re-processed can be used to perform quantitative measurements of the fluorescence light, with a high level of accuracy.

Third Image Processing Procedure

In a further example of embodiment, the control unit 120 is configured to execute a third image processing procedure that makes it possible to obtain wide field retinal images obtained with light reflected by the retina improved with respect to the wide field images that can be acquired directly by the control unit 120.

The aforesaid third processing procedure comprises a step of acquiring a retinal image obtained with light reflected by the retina.

Advantageously, this retinal image obtained with light reflected by the retina is acquired by the control unit 120 based on the information provided by the acquisition means 27.

For this acquisition, the first and second shaping means are arranged so that the light projection region 1141A, illuminated by the light beam 1, has a length Lil shorter than the length Lim of the light acquisition region 231A, from which the light beam 2 comes at least partially.

Moreover, a light source 121, 123, 124, 126 adapted to provide the type of light desired is appropriately activated and the filter means 28, if provided, are decoupled from the optical acquisition path 2A.

As illustrated above, the retinal image obtained with light reflected by the retina, as acquired, has a first light zone SI, having greater luminosity, and one or more second light zones SL having reduced luminosity (FIG. 14).

The aforesaid first processing procedure comprises a step of processing the retinal image obtained with light reflected by the retina, as acquired, to obtain first detection data indicative of the fluorescence light level of said second light zones SL.

The first detection data thus obtained are therefore indicative of the light level of the parasitic light present in the aforesaid retinal image obtained with light reflected by the retina, as acquired by the control unit 120.

Preferably, the aforesaid first detection data are obtained by measuring in several points the light level at these second zones SL.

The aforesaid third processing procedure comprises a step of receiving a wide field retinal image obtained with light reflected by the retina.

Advantageously, this wide field retinal image obtained with light reflected by the retina is acquired by the control unit 120 based on the information provided by the acquisition means 27.

For this acquisition, the first and second shaping means are arranged so that the light projection region 1141A, illuminated by the light beam 1, has a length Lil longer than or equal to the length Lim of the light acquisition region 231A from which the light beam 2 comes at least partially (FIG. 15).

Moreover, a light source 121, 123, 124, 126 adapted to provide the type of light desired is appropriately activated and any filter means 28 are decoupled from the optical acquisition path 2A.

As illustrated above, the wide field retinal image obtained with light reflected by the retina, as acquired, has a third light zone SFL (FIG. 15).

The aforesaid third processing procedure comprises a step of processing the aforesaid first wide field retinal image obtained with light reflected by the retina, as acquired, and the aforesaid first detection data to obtain a further wide field retinal image obtained with light reflected by the retina.

Preferably, in this processing step:
the first detection data are processed to obtain a parasitic light image indicative of the light level of the parasitic light present in the retinal image obtained with light reflected by the retina, originally acquired;
the parasitic light image is processed to obtain a wide field parasitic light image indicative of the light level of the parasitic light present in the wide field retinal image obtained with light reflected by the retina, as acquired;
the wide field parasitic light image, as constructed, is subtracted from the wide field retinal image obtained with light reflected by the retina, as acquired, to obtain a further wide field retinal image obtained with light reflected by the retina less disturbed by the brightness contribution of the unwanted parasitic light.

The further wide field retinal image, thus processed, has a reduction of the "blurring" effects caused by the parasitic light generated in zones of the apparatus 500 or of the eye 100 (in particular of the crystalline lens 103) that are not conjugated with the retina 101.

This further wide field retinal image obtained with light reflected by the retina has a higher contrast level, facilitating identification of any diseased retinal zones.

In a variant of embodiment thereof, in which the retina is illuminated activating a white light source and acquiring a wide field retinal image obtained with light reflected by the retina, analogously to what was illustrated for the first processing procedure described above, the aforesaid third image processing procedure comprises some steps to improve the colour tone of the further wide field retinal image obtained with light reflected by the retina.

Preferably, the third processing procedure comprises:
processing the aforesaid first detection data to obtain first estimation data indicative of the light absorption by the crystalline lens of the eye;
adjusting one or more colour channels of said further wide field retinal image obtained with light reflected by the retina based on said first estimation data.

The further wide field retinal image obtained with light reflected by the retina thus re-processed has colours that better reflect the natural colours of the retina.

Fourth Image Processing Procedure

In a further example of embodiment, the control unit 120 is configured to execute a fourth image processing procedure that that makes it possible to obtain improved wide field fluorescence retinal images with respect to the wide field fluorescence images that can be acquired directly by the control unit 120.

The aforesaid fourth processing procedure comprises a step of acquiring a fluorescence retinal image.

Advantageously, this fluorescence retinal image is acquired by the control unit 120 based on the information provided by the acquisition means 27.

For this acquisition, the first and second shaping means are arranged so that the light projection region 1141A, illuminated by the light beam 1, has a length Lil shorter than the length Lim of the light acquisition region 231A, from which the light beam 2 comes.

Moreover, a light source 126 capable of providing a suitable excitation light capable of exciting the fluorescent substances present on the retina is activated and the filter 31 is advantageously coupled to the optical acquisition path 2A.

The fluorescence retinal image, as acquired, has a first light zone SI, having greater luminosity, and one or more second light zones SL having reduced luminosity (FIG. 14).

The aforesaid fourth processing procedure comprises a step of processing the fluorescence retinal image, as acquired, to obtain second detection data indicative of the fluorescence light level at the aforesaid second light zones SL.

The second detection data thus obtained are indicative of the light level of the fluorescence parasitic light present in the aforesaid fluorescence retinal image, as acquired by the control unit 120.

Preferably, the aforesaid first detection data are obtained by measuring in several points the fluorescence light level at these second zones SL.

The aforesaid fourth processing procedure comprises a step of receiving a wide field fluorescence retinal image.

Advantageously, this wide field fluorescence retinal image is acquired by the control unit 120 based on the information provided by the acquisition means 27.

For this acquisition, the first and second shaping means are arranged so that the light projection region 1141A, illuminated by the light beam 1, has a length Lil longer than or equal to the length Lim of the light acquisition region 231A, from which the light beam 2 comes.

As illustrated above, the wide field fluorescence retinal image has a third light zone SFL (FIG. 15).

The aforesaid fourth processing procedure comprises a step of processing the wide field fluorescence retinal image and the aforesaid first detection data to obtain a further wide field fluorescence retinal image.

Preferably, in this processing step:
the first detection data are processed to obtain a parasitic light image indicative of the light level of the parasitic light present in the fluorescence retinal image, as acquired;
the parasitic light image is processed to obtain a wide field parasitic light image indicative of the light level of the fluorescence parasitic light present in the wide field fluorescence retinal image;
the wide field parasitic light image, as constructed, is subtracted from the wide field fluorescence retinal image, as acquired, to obtain a further wide field fluorescence retinal image that is less disturbed by the brightness contribution of the unwanted fluorescence parasitic light.

The further wide field fluorescence retinal image, thus processed, has a reduction of the "blurring" effects caused by the fluorescence parasitic light generated in zones of the apparatus 500 or of the eye 100 (in particular of the crystalline lens 103) that are not conjugated with the retina 101.

This further wide field fluorescence retinal image has greater contrast, facilitating identification of any diseased retinal zones.

In a variant of embodiment thereof, the fourth image processing procedure makes it possible to obtain wide field fluorescence images particularly useful for performing quantitative measurements of the fluorescence light emitted by the retina.

According to this variant of embodiment, the aforesaid second processing procedure comprises a step of acquiring a retinal image obtained with light reflected by the retina.

Advantageously, this retinal image obtained with light reflected by the retina is acquired by the control unit 120 based on the information provided by the acquisition means 27.

For this acquisition, the first and second shaping means are arranged so that the light projection region 1141A, illuminated by the light beam 1, has a length Lil shorter than the length Lim of the light acquisition region 231A, from which the light beam 2 comes.

A first preferred solution to obtain the retinal image obtained with light reflected by the retina is to activate the excitation source 126 and acquire the retinal image with the filter means 28 decoupled from the acquisition path 2A.

A second preferred solution is to acquire a retinal image obtained with light reflected by the retina activating a source 121, 123, 124 capable of projecting white light with the filter means 28 decoupled from the acquisition path 2A.

The aforesaid retinal image obtained with light reflected by the retina has a first light zone SI, having greater luminosity, and one or more second light zones SL having reduced luminosity (FIG. 14).

The aforesaid fourth processing procedure comprises a step of processing the retinal image obtained with light reflected by the retina, as acquired; to obtain first detection data indicative of the fluorescence light level of said second light zones SL.

The first detection data thus obtained are indicative of the light level of the parasitic light present in the aforesaid retinal image obtained with light reflected by the retina, as acquired by the control unit 120.

Therefore, the aforesaid fourth processing procedure comprises the following steps:
processing the first detection data to obtain second estimation data indicative of the level of opacity of the crystalline lens of the eye to excitation light;
processing said second estimation data to obtain third estimation data indicative of a level of fluorescence light absorption by the crystalline lens of the eye;
adjusting the brightness of said further wide field fluorescence retinal image based on said second and third estimation data.

By appropriately processing the first detection data indicative of the fluorescence light level of said second light zones SL of the retinal image obtained with light reflected by the retina, as acquired, it is possible to estimate the level of opacity of the crystalline lens and, consequently, obtain second estimation data indicative of the capacity of excitation light absorption (light beam 1) by the crystalline lens.

Based on the aforesaid second estimation data, indicative of the capacity of excitation light absorption by the crystalline lens, it is possible to adjust the brightness of the further wide field fluorescence retinal image processed, to offset attenuation of the excitation light caused by the crystalline lens.

By appropriately processing the first detection data indicative of the fluorescence light level of said second light zones SL of the aforesaid first retinal image obtained with light reflected by the retina, it is possible to estimate the level of opacity of the crystalline lens and, consequently, obtain third estimation data regarding the capacity of fluorescence retinal light absorption (light beam 2) by the crystalline lens.

Based on the aforesaid third estimation data indicative of the capacity of fluorescence light absorption by the crystalline lens, it is possible to adjust the brightness of the further wide field fluorescence retinal image to offset attenuation of the fluorescence light caused by the crystalline lens.

The further wide field fluorescence retinal image thus re-processed can be used to perform quantitative measurements of the fluorescence light with a high level of accuracy.

The apparatus 500 according to the invention has considerable advantages with respect to prior art.

The production of the first and second light beam shaping means arranged to obtain a light projection region 1141A with length shorter than the light acquisition region 231A makes it possible to obtain improved retinal images (obtained with light reflected by the retina or fluorescence light—if necessary also wide field) with a high level of contrast, more natural colour tones, brightness influenced to a lesser extent by parasitic light generated or scattered by the crystalline lens and by light absorption by the crystalline lens and a lower probability of artifacts.

The apparatus 500 has a very compact structure and is easy to produce on an industrial scale, with considerable advantages in terms of limiting production costs.

The invention claimed is:

1. An eye fundus inspection apparatus, comprising:
   illumination means comprising at least a light source and adapted to project a first light beam towards a retina of an eye via an optical lighting path;
   acquisition means adapted to receive a second light beam coming from the retina via an optical acquisition path;
   scanning means adapted to scan said first light beam on the retina with a linear movement according to a rectilinear first scanning direction, or with a circular movement about a rotation axis according to a circular second scanning direction;
   light beam separating means adapted to define separated passage zones for said first and second light beams at a pupil of the eye;
   first light beam shaping means adapted to provide a first passage section for said first light beam along said optical lighting path,
      said first passage section being arranged in a position optically conjugated with the retina and defining, on the retina, a light projection region at which said first light beam is projected on the retina,
      said light projection region having a linear shape with a length measured along a direction perpendicular to said first scanning direction or along a direction radial to said second scanning direction and a width measured along a direction parallel to said first scanning direction or along a direction tangential to said second scanning direction;
   second light beam shaping means adapted to provide a second passage section for said second light beam along said optical acquisition path,
      said second passage section being arranged in a position optically conjugated with the retina and defining, on the retina, a light acquisition region from which said second light beam comes at least partially,
      said light acquisition region having a linear shape with a length measured along a direction perpendicular to said first scanning direction or along a direction radial to said second scanning direction and a width measured along a direction parallel to said first scanning direction or along a direction tangential to said second scanning direction;
   said light projection region and said light acquisition region at least partially overlapping one another and moving synchronously with respect to the retina according to said first scanning direction or said second scanning direction, said light projection region having a length shorter than the length of said light acquisition region.

2. The eye fundus inspection apparatus of claim 1, wherein:
   said first light beam shaping means are also adapted to provide a third passage section for said first light beam along said optical lighting path,
   said third passage section being arranged in a position optically conjugated with the retina and defining, on the retina, a further light projection region at which said first light beam is projected on the retina,
   said further light projection region having a linear shape with a length measured along a direction perpendicular to said first scanning direction or along a direction radial to said second scanning direction and a width measured along a direction parallel to said first scanning direction or along a direction tangential to said second scanning direction,
   said further light projection region having a length larger than or equal to the length of said light acquisition region.

3. The eye fundus inspection apparatus of claim 2, wherein:
   said first light beam shaping means comprise a projection diaphragm,
   said projection diaphragm comprising a first projection opening adapted to define said first passage section for said first light beam and a second projection opening adapted to define said third passage section for said first light beam,
   said projection diaphragm being movable between at least a first coupling position with said optical lighting path, at which said first projection opening is optically coupled with said optical lighting path, and a second coupling position with said optical lighting path, at which said second projection opening is coupled with said optical lighting path.

4. The eye fundus inspection apparatus of claim 2, wherein:
   said first light beam shaping means comprise a projection diaphragm,
   said projection diaphragm comprising a second projection opening adapted to define said third passage section for said first light beam,
   said projection diaphragm being operatively coupled with a mask movable in a first masking position, at which said mask does not cover said second projection opening, and in a second masking position, at which said mask partially covers said second projection opening to obtain a first projection opening adapted to define said first passage section for said first light beam.

5. The eye fundus inspection apparatus of claim 1, wherein:
   said second light beam shaping means comprise a confocal diaphragm comprising a confocal opening adapted to define said second passage section for said second light beam.

6. The eye fundus inspection apparatus of claim 1, further comprising a control unit adapted to control operation of said inspection apparatus, and wherein:
   said second light beam shaping means comprise a light receiving surface of said acquisition means;
   said light receiving surface comprises one or more surface portions that can be selectively activated by said control unit; and
   each surface portion, when activated by said control unit, is adapted to define said second passage section for said second light beam.

7. The eye fundus inspection apparatus of claim 1, wherein:
   said second light beam shaping means comprise at least a light receiving surface portion of a TDI sensor of said acquisition means,
   said at least a light receiving surface portion being adapted to define said second passage section for said second light beam.

8. The eye fundus inspection apparatus of claim 1, wherein:
   said illumination means comprise an excitation light source capable of exciting fluorescent substances on the retina and optically coupled with said optical lighting path,
   said inspection apparatus comprising first filtering means of said second light beam arranged along said optical acquisition path.

9. The eye fundus inspection apparatus of claim 8, wherein:
said first filtering means comprise a filter movable between a coupling position and a decoupling position with said optical acquisition path.

10. The eye fundus inspection apparatus of claim 1, further comprising a control unit adapted to acquire at least a retinal image having a first light zone corresponding to a first retinal area travelled by said light projection region during a synchronous movement of said light projection region and said light acquisition region with respect to the retina and one or more second light zones corresponding to one or more third retinal areas travelled by one or more non-overlapping portions between said light projection region and said light acquisition region during the synchronous movement of said light projection region and said light acquisition region with respect to the retina.

11. The eye fundus inspection apparatus of claim 10, wherein said control unit is further configured to:
acquire a fluorescence retinal image, said fluorescence retinal image having said first light zone and said second light zones;
process said fluorescence retinal image to obtain second detection data indicative of the fluorescence light level of said second light zones; and
process said fluorescence retinal image and said second detection data to obtain a further fluorescence retinal image.

12. The eye fundus inspection apparatus of claim 11, wherein said control unit is further configured to:
acquire a retinal image obtained with light reflected by the retina, said retinal image obtained with light reflected by the retina having said first light zone and said second light zones;
process said retinal image obtained with light reflected by the retina to obtain first detection data indicative of the light level of said second light zones;
process said first detection data to obtain second estimation data indicative of a level of opacity of the crystalline lens of the eye to an excitation light projected on the retina;
process said second estimation data to obtain third estimation data indicative of a level of fluorescence light absorption by the crystalline lens of the eye; and
adjust the brightness of said further fluorescence retinal image based on said second and third estimation data.

13. The eye fundus inspection apparatus of claim 1, further comprising a control unit adapted to acquire at least a wide field retinal image having a third light zone corresponding to a third retinal area travelled by said light projection region during a synchronous movement of said light projection region and said light acquisition region with respect to the retina.

14. The eye fundus inspection apparatus of claim 13, wherein said control unit is further configured to:
acquire a retinal image obtained with light reflected by the retina, said retinal image obtained with light reflected by the retina having said first light zone and said second light zones;
process said retinal image obtained with light reflected by the retina to obtain first detection data indicative of the light level of said second light zones; and
process said retinal image obtained with light reflected by the retina and said first detection data to obtain a further retinal image obtained with light reflected by the retina.

15. The eye fundus inspection apparatus of claim 14, wherein said control unit is further configured to:
process said first detection data to obtain first estimation data indicative of light absorption by the crystalline lens of the eye; and
adjust one or more colour channels of said further retinal image obtained with light reflected by the retina based on said first estimation data.

16. The eye fundus inspection apparatus of claim 13, wherein said control unit is further configured to:
acquire a retinal image obtained with light reflected by the retina, said retinal image obtained with light reflected by the retina having said first light zone and said second light zones;
process said retinal image obtained with light reflected by the retina to obtain first detection data indicative of the light level of said second light zones;
acquire a wide field retinal image obtained with light reflected by the retina, said wide field retinal image obtained with light reflected by the retina having said third light zone; and
process said wide field retinal image obtained with light reflected by the retina and said first detection data to obtain a further wide field retinal image obtained with light reflected by the retina.

17. The eye fundus inspection apparatus of claim 16, wherein said control unit is further configured to:
process said first detection data to obtain first estimation data indicative of the light absorption by the crystalline lens of the eye; and
adjust one or more colour channels of said further wide field retinal image obtained with light reflected by the retina based on said first estimation data.

18. The eye fundus inspection apparatus of claim 13, wherein said control unit is further configured to:
acquire a fluorescence retinal image, said fluorescence retinal image having said first light zone and said second light zones;
process said fluorescence retinal image to obtain second detection data indicative of the fluorescence light level of said second light zones;
acquire a wide field fluorescence retinal image, said wide field fluorescence retinal image having said third light zone; and
process said wide field fluorescence retinal image and said second detection data to obtain a further wide field fluorescence retinal image.

19. The eye fundus inspection apparatus of claim 18, wherein said control unit is further configured to:
acquire a retinal image obtained with light reflected by the retina, said retinal image obtained with light reflected by the retina having said first light zone and said second light zones;
process said retinal image obtained with light reflected by the retina to obtain first detection data indicative of the light level of said second light zones;
process said first detection data to obtain second estimation data indicative of a level of opacity of the crystalline lens of the eye to an excitation light used to illuminate the retina;
process said second estimation data to obtain third estimation data indicative of a level of fluorescence light absorption by the crystalline lens of the eye; and
adjust the brightness of said further wide field fluorescence retinal image based on said second and third estimation data.

20. A method comprising:
projecting a first light beam from at least a light source towards a retina of an eye via an optical lighting path;

receiving a second light beam coming from the retina via an optical acquisition path;

scanning said first light beam on the retina with a linear movement according to a rectilinear first scanning direction, or with a circular movement about a rotation axis according to a circular second scanning direction;

separating the first light beam from the second light beam at a pupil of the eye;

providing a first passage section for said first light beam along said optical lighting path, said first passage section being arranged in a position optically conjugated with the retina and defining, on the retina, a light projection region at which said first light beam is projected on the retina, said light projection region having a linear shape with a length measured along a direction perpendicular to said first scanning direction or along a direction radial to said second scanning direction and a width measured along a direction parallel to said first scanning direction or along a direction tangential to said second scanning direction;

providing a second passage section for said second light beam along said optical acquisition path, said second passage section being arranged in a position optically conjugated with the retina and defining, on the retina, a light acquisition region from which said second light beam comes at least partially, said light acquisition region having a linear shape with a length measured along a direction perpendicular to said first scanning direction or along a direction radial to said second scanning direction and a width measured along a direction parallel to said first scanning direction or along a direction tangential to said second scanning direction;

wherein said light projection region and said light acquisition region at least partially overlap one another and move synchronously with respect to the retina according to said first scanning direction or said second scanning direction, said light projection region having a length shorter than the length of said light acquisition region.

* * * * *